(12) United States Patent
Wang et al.

(10) Patent No.: US 9,060,905 B2
(45) Date of Patent: Jun. 23, 2015

(54) WEARABLE ABSORBENT ARTICLES

(71) Applicant: The Procter & Gamble Company, Cincinnati, OH (US)

(72) Inventors: Samantha Chen-Yee Wang, Cincinnati, OH (US); Donald Carroll Roe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 151 days.

(21) Appl. No.: 13/789,709

(22) Filed: Mar. 8, 2013

(65) Prior Publication Data

US 2014/0257226 A1     Sep. 11, 2014

(51) Int. Cl.
| | | |
|---|---|---|
| A61F 13/15 | (2006.01) | |
| A61F 13/539 | (2006.01) | |
| A61F 13/505 | (2006.01) | |
| A61F 13/49 | (2006.01) | |
| A61F 13/496 | (2006.01) | |

(52) U.S. Cl.
CPC ............ *A61F 13/539* (2013.01); *A61F 13/505* (2013.01); *A61F 13/15268* (2013.01); *A61F 2013/5055* (2013.01); *A61F 13/49003* (2013.01); *A61F 13/49006* (2013.01); *A61F 13/4906* (2013.01); *A61F 13/496* (2013.01)

(58) Field of Classification Search
CPC ............ A61F 13/505; A61F 13/15268; A61F 13/4906; A61F 13/49061; A61F 2013/5055
USPC ............ 604/385.14, 385.15, 385.16, 385.24, 604/385.29
See application file for complete search history.

(56) References Cited

U.S. PATENT DOCUMENTS

| | | |
|---|---|---|
| 2,119,610 A | 6/1938 | Robert |
| 2,530,647 A | 11/1950 | Buchler |
| 2,688,328 A | 9/1954 | Marcus |
| 2,793,642 A | 5/1957 | Andruhovici |
| 3,077,193 A | 2/1963 | Mann |
| 3,496,259 A | 2/1970 | Guenther |
| 3,560,292 A | 2/1971 | Butter |

(Continued)

FOREIGN PATENT DOCUMENTS

| | | |
|---|---|---|
| AU | 642 386 | 10/1993 |
| CA | 2 103 537 | 2/1995 |

(Continued)

OTHER PUBLICATIONS www.gdiapers.com—Web pages dated Nov. 23, 2009.

(Continued)

*Primary Examiner* — Jacqueline Stephens
(74) *Attorney, Agent, or Firm* — Christian M. Best

(57) ABSTRACT

A wearable absorbent article comprises a reusable outer cover and a disposable absorbent insert. The reusable outer cover comprises a first insert fastener component in a front waist region proximate to a waist opening edge of the reusable outer cover. The first insert fastener component comprises a first end positioned most proximate to the waist opening edge and a second end positioned most distal from the waist opening edge. An insert-gripping recess is formed in the first end in an area covering a longitudinal axis of the reusable outer cover. The disposable absorbent insert comprises a first fastener component in a forward region of the insert and configured to be joined to the first insert fastener component to attach the insert to the reusable outer cover.

22 Claims, 24 Drawing Sheets

(56) References Cited

U.S. PATENT DOCUMENTS

| | | |
|---|---|---|
| 3,719,736 A | 3/1973 | Woodruff |
| 3,735,424 A | 5/1973 | Maggio et al. |
| 3,860,003 A | 1/1975 | Buell |
| 3,911,173 A | 10/1975 | Sprague, Jr. |
| 3,926,189 A | 12/1975 | Taylor |
| 3,929,135 A | 12/1975 | Thompson |
| 3,955,575 A | 5/1976 | Okuda |
| 4,022,210 A | 5/1977 | Glassman |
| 4,072,150 A | 2/1978 | Glassman |
| 4,081,301 A | 3/1978 | Buell |
| 4,116,892 A | 9/1978 | Schwarz |
| 4,195,634 A | 4/1980 | DiSalvo et al. |
| 4,223,059 A | 9/1980 | Schwarz |
| 4,265,245 A | 5/1981 | Glassman |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | Mcfarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,625,245 A | 11/1986 | White |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,704,116 A | 11/1987 | Enloe |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,283,910 A | 2/1994 | Flint |
| 5,290,270 A | 3/1994 | Fisher |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,509,915 A | 4/1996 | Hanson et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A | 3/1997 | Roessler et al. |
| 5,624,425 A | 4/1997 | Gray et al. |
| 5,624,429 A | 4/1997 | Long et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kj.ae butted.rgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| 5,846,232 A | 12/1998 | Serbiak et al. |
| H1788 H | 2/1999 | Christon et al. |
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 5,984,911 A | 11/1999 | Siebers et al. |

(56) References Cited

U.S. PATENT DOCUMENTS

| | | | |
|---|---|---|---|
| 6,007,528 A | 12/1999 | Osborn |
| 6,010,491 A | 1/2000 | Roe et al. |
| 6,120,487 A | 9/2000 | Ashton |
| 6,142,983 A | 11/2000 | Suprise et al. |
| 6,207,738 B1 | 3/2001 | Zuckerman et al. |
| 6,213,991 B1 | 4/2001 | Kling et al. |
| 6,229,061 B1 | 5/2001 | Draggo et al. |
| 6,240,569 B1 | 6/2001 | Van Gompel et al. |
| 6,251,097 B1 | 6/2001 | Kline et al. |
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,623,466 B1 | 9/2003 | Richardson |
| 6,669,618 B2 | 12/2003 | Reising et al. |
| 6,680,422 B2 | 1/2004 | Roe |
| 6,709,423 B1 | 3/2004 | Herrlein et al. |
| 6,716,441 B1 | 4/2004 | Osborne et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,921,393 B2 | 7/2005 | Tears et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,166,095 B1 | 1/2007 | Coates |
| 7,175,613 B2 | 2/2007 | Sugiyama et al. |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Franke et al. |
| 7,537,587 B2 | 5/2009 | Carstens |
| 7,576,019 B2 | 8/2009 | Bond et al. |
| 7,591,811 B2 | 9/2009 | Wilkinson |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,820,875 B2 | 10/2010 | Roe et al. |
| 7,824,387 B2 | 11/2010 | LaVon |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,985,210 B2 | 7/2011 | Ashton et al. |
| 7,993,322 B2 | 8/2011 | Brud et al. |
| 8,062,276 B2 | 11/2011 | Labit et al. |
| 8,066,685 B2 | 11/2011 | Olson et al. |
| 8,118,801 B2 | 2/2012 | Macura et al. |
| 8,158,043 B2 | 4/2012 | Gibson et al. |
| 8,206,366 B2 | 6/2012 | Datta et al. |
| 8,262,635 B2 | 9/2012 | Labit et al. |
| 8,377,023 B2 | 2/2013 | Sawyer et al. |
| 8,568,380 B2 | 10/2013 | Brownlee |
| 8,585,667 B2 | 11/2013 | Roe et al. |
| 2002/0010452 A1 | 1/2002 | Dupuy |
| 2002/0035747 A1 | 3/2002 | Kusibojoska et al. |
| 2002/0045874 A1 | 4/2002 | Kumasaka et al. |
| 2002/0076520 A1 | 6/2002 | Neeb et al. |
| 2002/0128619 A1 | 9/2002 | Carlbark et al. |
| 2003/0055394 A1 | 3/2003 | Gibbs |
| 2003/0088220 A1 | 5/2003 | Molander et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0030311 A1 | 2/2004 | Suzuki et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0164587 A1 | 7/2005 | Melik et al. |
| 2005/0175269 A1 | 8/2005 | Ashton et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2005/0234419 A1* | 10/2005 | Kline et al. .................. 604/378 |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakravarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0247599 A1 | 11/2006 | Mullen et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |

(56) References Cited

U.S. PATENT DOCUMENTS

| | | |
|---|---|---|
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |
| 2007/0142798 A1 | 6/2007 | Goodlander et al. |
| 2007/0142816 A1 | 6/2007 | Carstens |
| 2007/0191806 A1 | 8/2007 | Mueller et al. |
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdon et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0081854 A1 | 4/2008 | Wang et al. |
| 2008/0108963 A1 | 5/2008 | Ashton et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0188822 A1 | 8/2008 | Lodge et al. |
| 2008/0215027 A1 | 9/2008 | Labit et al. |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0137277 A1 | 6/2011 | Hough et al. |
| 2011/0172622 A1 | 7/2011 | Roe et al. |
| 2011/0288518 A1 | 11/2011 | Roe et al. |
| 2012/0022485 A1 | 1/2012 | Roe et al. |
| 2012/0022491 A1 | 1/2012 | Roe |
| 2012/0049404 A1 | 3/2012 | Gibson et al. |
| 2013/0102986 A1 | 4/2013 | Ruiz et al. |
| 2013/0226122 A1 | 8/2013 | Roe et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 | 11/2003 |
| EP | 0 023 804 | 2/1981 |
| EP | 0 187 726 | 7/1986 |
| EP | 319314 | 6/1989 |
| EP | 0667136 | 8/1995 |
| EP | 549988 | 6/1998 |
| EP | 796069 | 8/2000 |
| EP | 763353 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | H11104180 | 4/1999 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-94/15663 | 7/1994 |
| WO | WO-95/10992 | 4/1995 |
| WO | WO-95/16746 | 6/1995 |
| WO | WO-96/17572 | 6/1996 |
| WO | WO-96/24319 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |

(56) References Cited

FOREIGN PATENT DOCUMENTS

| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 | 3/2008 |
| WO | WO-2008/120959 | 10/2008 |
| WO | WO-2008/142634 | 11/2008 |
| WO | WO-2010/053006 | 5/2010 |
| WO | WO-2010/078661 | 7/2010 |
| WO | WO-2012/167844 | 12/2012 |
| WO | WO-2013/059533 | 4/2013 |

OTHER PUBLICATIONS www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
All Office Actions, U.S. Appl. No. 13/789,707.
All Office Actions, U.S. Appl. No. 13/789,711.
All Office Actions, U.S. Appl. No. 13/789,731.
All Office Actions, U.S. Appl. No. 13/789,735.
All Office Actions, U.S. Appl. No. 13/789,738.
International Search Report and Written Opinion, PCT/US2014/020806, date of mailing May 21, 2014.
US 5,583,910, 12/1996, Flint (withdrawn).

\* cited by examiner

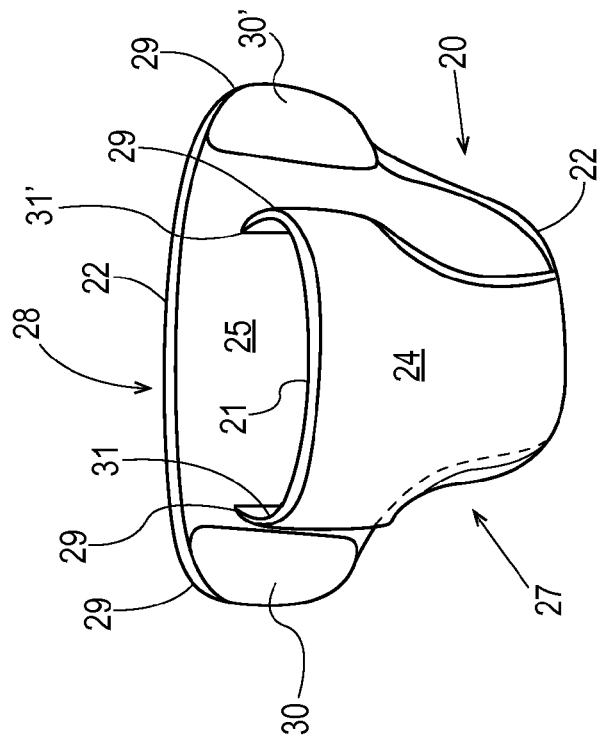
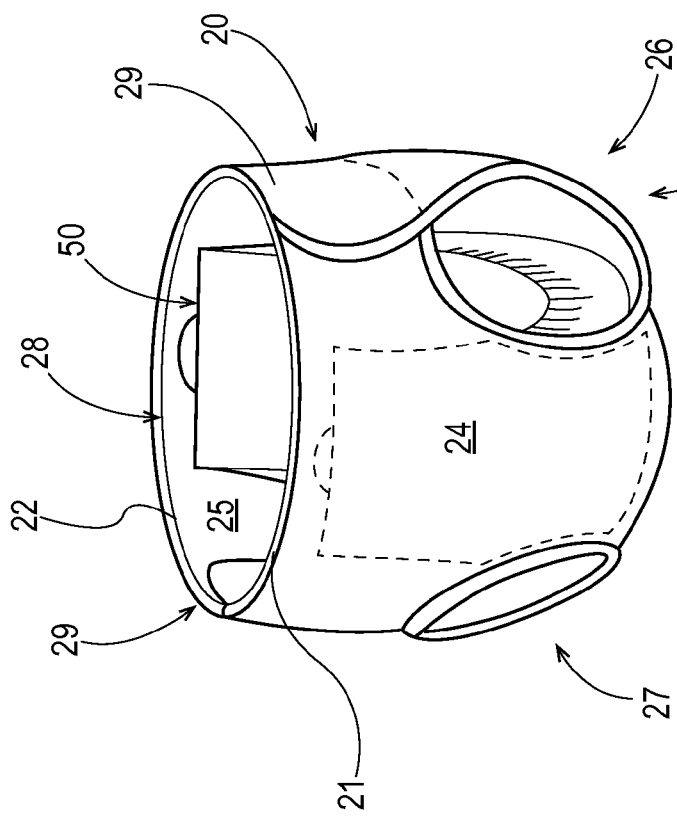

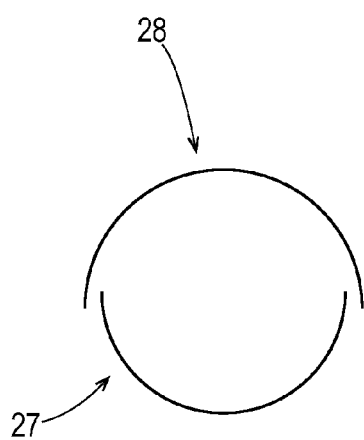 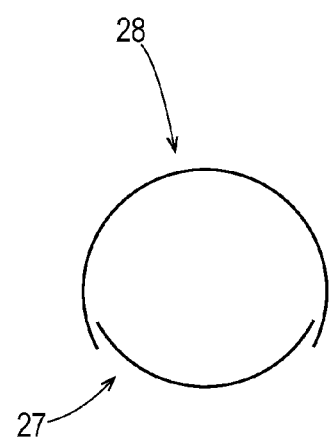 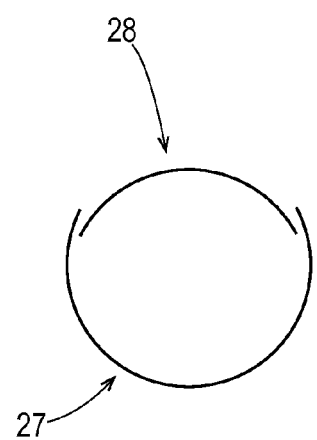
Fig. 1E    Fig. 1F    Fig. 1G
 
Fig. 1H    Fig. 1I

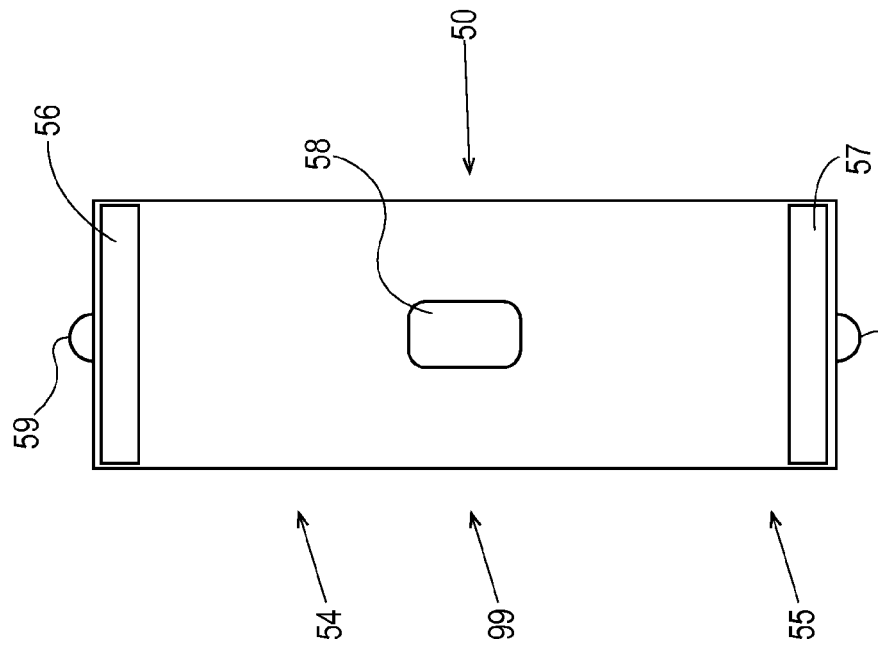
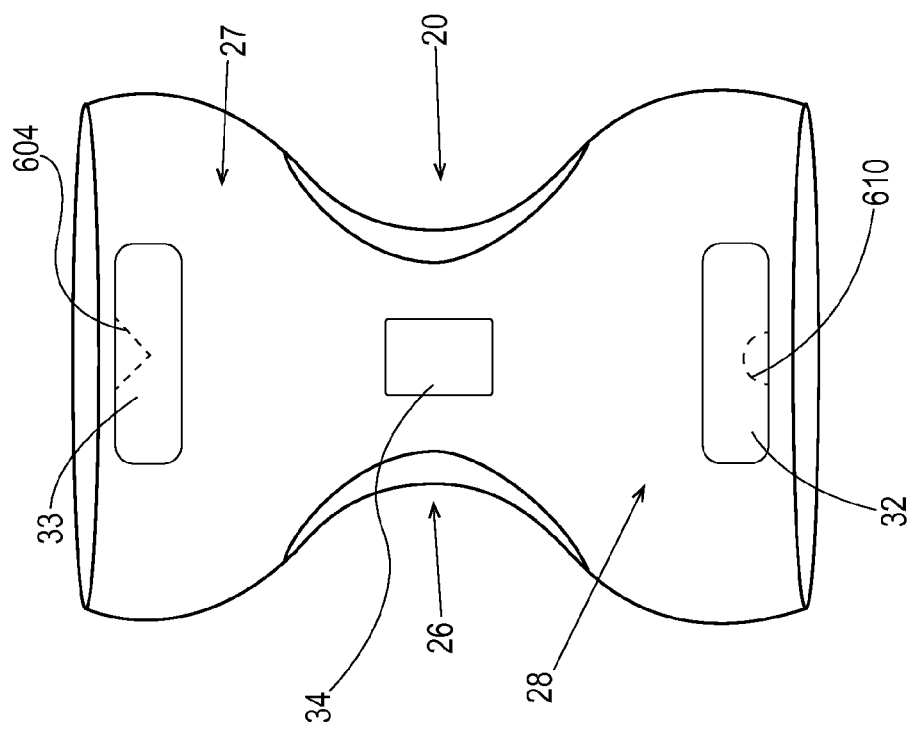

WEARABLE ABSORBENT ARTICLES

FIELD

The present disclosure relates generally to the field of wearable absorbent articles having features for the containment and absorption of bodily exudates, and more particularly, to such articles having disposable absorbent inserts and reusable outer covers, wherein the reusable outer covers and disposable absorbent inserts have certain fastener component configurations.

BACKGROUND

In general, disposable absorbent inserts may be engaged with reusable outer covers to form wearable absorbent articles, such as a taped diaper, a pant, or an adult incontinence product. The outer covers may comprise one or more insert fastener components configured to be engaged with one or more fastener components on disposable absorbent inserts. While various fastener component configurations between an insert and an outer cover are generally known, improved fastener component configurations should be developed. Especially important are fastener component configurations that allow for attachment of the disposable absorbent insert to the reusable outer cover when the reusable outer cover is in the form of a closed waist pant or a closed waist adult incontinence product.

SUMMARY

In an embodiment, the present disclosure is directed, in part, to a wearable absorbent article comprising a reusable outer cover and a disposable absorbent insert. The reusable outer cover may comprise a front waist region, a rear waist region, and a crotch region disposed intermediate the front waist region and the rear waist region. The reusable outer cover may further comprise a waist opening edge and a first insert fastener component in the front waist region proximate to the waist opening edge. The first insert fastener component may comprise a first end positioned most proximate to the waist opening edge and a second end positioned most distal from the waist opening edge. An insert-gripping recess may be formed in the first end in an area covering a longitudinal axis of the reusable outer cover. The reusable outer cover may further comprise a second insert fastener component in the rear waist region proximate to the waist opening edge. The disposable absorbent insert may comprise a forward region, a rearward region, and a crotch region disposed intermediate the forward region and the rearward region. The disposable absorbent insert may further comprise a first fastener component in the forward region configured to be joined to the first insert fastener component to attach the insert to the reusable outer cover and a second fastener component in the rearward region configured to be joined to the second insert fastener component to attach the insert to the reusable outer cover.

In an embodiment, the present disclosure is directed, in part, to a wearable absorbent article comprising a reusable outer cover and a disposable absorbent insert. The reusable outer cover may comprise a front waist region, a rear waist region, and a crotch region disposed intermediate the front waist region and the rear waist region. The reusable outer cover may further comprise a first insert fastener component in the front waist region, a second insert fastener component in the rear waist region, and a third insert fastener component in the crotch region. The disposable absorbent insert may comprise a forward region, a rearward region, and a crotch region disposed intermediate the forward region and the rearward region. The disposable absorbent insert may further comprise a first fastener component in the forward region configured to be joined to the first insert fastener component, a second fastener component in the rearward region configured to be joined to the second insert fastener component, and a third fastener component in the crotch region configured to be joined to the third insert fastener component. The third insert fastener component and the third fastener component may together form a self-aligning fastener, a discrete fastener, or an adjustable fastener.

In an embodiment, the present disclosure is directed, in part, to a wearable absorbent article comprising a reusable outer cover and a disposable absorbent insert. The reusable outer cover may comprise a front waist region, a rear waist region, and a crotch region disposed intermediate the front waist region and the rear waist region. The reusable outer cover may further comprise a first insert fastener component in the front waist region, a second insert fastener component in the rear waist region, and a third insert fastener component in the crotch region. The disposable absorbent insert may comprise a forward region, a rearward region, and a crotch region disposed intermediate the forward region and the rearward region. The disposable absorbent insert may further comprise a first fastener component in the forward region configured to be joined to the first insert fastener component. The first insert fastener component and the first fastener component may together form a self-aligning fastener, a discrete fastener, or an adjustable fastener. The disposable absorbent insert may further comprise a second fastener component in the rearward region configured to be joined to the second insert fastener component. The second insert fastener component and the second fastener component may together form a self-aligning fastener, a discrete fastener, or an adjustable fastener. The disposable absorbent insert may further comprise a third fastener component in the crotch region configured to be joined to the second insert fastener component. The third insert fastener component and the third fastener component may together form a discrete fastener, a self-aligning fastener, or an adjustable fastener. The first insert fastener component may form an insert-gripping recess therein.

BRIEF DESCRIPTION OF THE DRAWINGS

FIG. 1C is a perspective view of a wearable absorbent article with the fastening zones in a closed configuration and with a disposable absorbent insert positioned therein in accordance with a non-limiting embodiment of the present disclosure;

FIG. 1D is a perspective view of the wearable absorbent article of FIG. 1C with the fastening zones in an open configuration in accordance with a non-limiting embodiment of the present disclosure;

FIG. 1E is an illustration of a waist region of a pant having fastening zones on the sides in accordance with a non-limiting embodiment of the present disclosure;

FIG. 1F is an illustration of a waist region of a pant having fastening zones in the front waist region in accordance with a non-limiting embodiment of the present disclosure;

FIG. 1G is an illustration of a waist region of a pant having fastening zones in the rear waist region in accordance with a non-limiting embodiment of the present disclosure;

FIG. 1H is an illustration of an overlap seam in a fastening zone in accordance with a non-limiting embodiment of the present disclosure;

FIG. 1I is an illustration of a butt seam in a fastening zone in accordance with a non-limiting embodiment of the present disclosure;

FIG. 17 is a plan view of a reusable outer cover opened and laid flat, inner, wearer-facing surface oriented towards the viewer in accordance with a non-limiting embodiment of the present disclosure; and FIG. 18 is a plan view of a disposable absorbent insert opened and laid flat, outer, garment-facing surface oriented towards the viewer in accordance with a non-limiting embodiment of the present disclosure.

DETAILED DESCRIPTION

Definitions

Figure 1A:
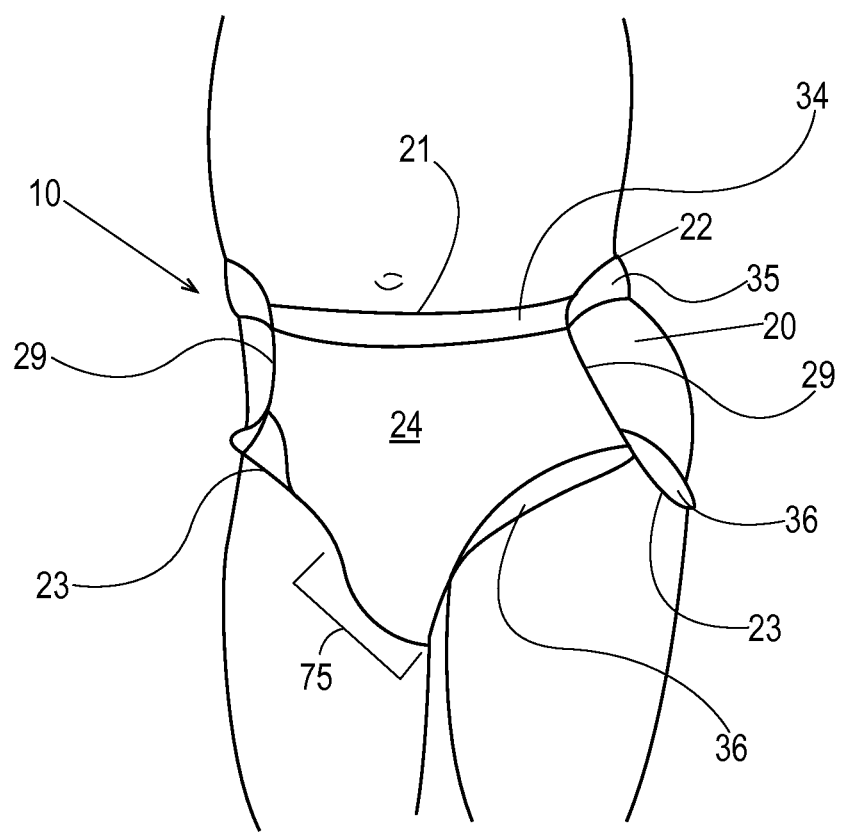
FIG. 1A is a perspective view of a wearable absorbent article as it might appear being worn by a wearer about the lower torso in accordance with a non-limiting embodiment of the present disclosure.

For purposes of this description, the following terms have the meanings set forth:

"Absorbent insert" and "insert" mean a component of a wearable absorbent article that is configured to contain and/or absorb urine, feces, menses, or any combination thereof, and is configured to be installed and removed as a modular unit, from a reusable outer cover. The insert may or may not comprise an absorbent core.

"Attachment zone" means one or more fastener components positioned on or formed on the inner surface of the outer cover which are used to removably attach or join an insert to an outer cover. The fastener components of the attachment zone may be hooks, loops, adhesives, cohesive, snaps, buttons, pockets, and/or any other suitable fastener components known to one of skill in the art.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Fastening zone" means an area of fastening, attachment, or joining of a portion of an outer cover (e.g., a portion in a front waist region) to another portion of the outer cover (e.g., a portion in a rear waist region) to form a seam. The fastening, attachment, or joining, may be permanent, releasable, or refastenable. The fastening zones may each form a seam, such as an overlap seam or a butt seam, configured to join a portion of a front waist region to a portion of a rear waist region. An outer cover may comprise one or more fastening zones. Each portion of each fastening zones described herein may extend, at least in part, in the longitudinal direction (i.e., parallel to the longitudinal axis of the outer cover) or in generally the longitudinal direction (e.g., +/−20 degrees from the longitudinal axis). Each portion of each fastening zone may also extend in the lateral direction or in generally the lateral direction.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse, across, or perpendicular to the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along or parallel to the component as it would be properly situated on a wearer, from the front to the rear of the wearer, or vice versa.

"Outer cover" means a component of a wearable absorbent article that is configured to be worn about the lower torso of a wearer, and that is configured to support an insert and hold the insert next to the wearer's body. The outer cover may be attached to the insert through the use of attachment zones on the insert and attachment zones on the insert. The outer cover may form a pant or may be configured to form a pant by attaching or joining portions of the fastening zones together. Herein, an outer cover may also be referred to as a "chassis". The terms "outer cover" and "chassis" are interchangeable for purposes herein, and include, but are not limited to, garments having features as described herein and configured as diapers, diaper covers, underpants, briefs, training pants, boxer shorts, pants, and/shorts, for example.

"Pant" means a wearable absorbent article having a continuous perimeter waist opening and continuous perimeter leg openings in an outer cover thereof designed for infant, child, or adult wearers (e.g., adult incontinence). A pant may be configured with a continuous or closed waist opening and at least one or two continuous, closed, leg openings prior to the article being applied to the wearer. In other embodiments, a pant may be configured with an open waist opening and open leg openings prior to the article being applied to the wearer. A pant may be preformed (e.g., by a manufacturer or a user) by various techniques including, but not limited to, joining together portions of fastening zones of an outer cover or using any refastenable and/or permanent closure member (e.g., seams, heat bonds, pressure welds, adhesives, cohesive bonds, mechanical fasteners, etc.). A pant may be preformed anywhere along the circumference of the wearable absorbent article in the waist region (e.g., side fastened or seamed, front waist fastened or seamed, rear waist fastened or seamed). A pant may be opened about one or both of the seams and then refastened and/or readjusted. Pants having fasteners in fastening zones of the outer cover that form the circumference may be joined at the sides, in the front waist region, and/or in the rear waist region. A pant is formed by an outer cover and an absorbent insert, when the absorbent insert is joined with the outer cover. To be classified as a pant, the absorbent article should be designed such that when in a closed configuration (i.e., the waist and leg openings have a continuous circumference), the pant may be pulled up over the wearer's thighs and buttocks to the waist. Pants should have sufficient stretch and/or extension to enable such pulling up over the thighs and buttocks all while not having such a wide waist such that the pant falls down on smaller wearers once pulled up. These features, among others, differentiate pants from and taped diapers that are wrapped around the wearer when the wearer is laying down and not "pulled up". In some embodiments, the pant, when in an open (or partially open (e.g., one closed leg opening)) configuration, may be applied to a standing wearer.

"Reusable", when referring to an outer cover, means an outer cover that is configured to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Taped diaper" means a wearable absorbent article comprising an outer cover having an initial front waist region and an initial rear waist region that are not fastened, pre-fastened, or connected to each other, prior to being applied to the wearer. The taped diaper may also include an insert joined to the outer cover through the use of attachment zones on the outer cover and the insert. A taped diaper may be folded about its lateral central axis with the interior of one waist region in surface to surface contact with the interior of the opposing waist region without fastening or joining the waist regions together.

"Use," with respect to an outer cover, means one event of the wearing of the outer cover until the time an insert is replaced.

"User" means a caregiver or other person who may apply a wearable absorbent article to a wearer. Where the wearer is capable of donning the wearable absorbent article him/herself, the wearer is also a "user".

"Wearer" means a person who may wear the wearable absorbent article described herein.

"Wearable absorbent article" means any article designed to be worn about the lower torso and to contain and/or absorb urine, feces, menses, or any combination thereof "Wearable absorbent article" includes, but is not limited to, baby or children's diapers (of the "tape"-fastenable, otherwise fastenable, "pull-up" or any other variety), training pants and adult incontinence pants, briefs, and the like.

Fastening zones having particular configurations are provided by the present disclosure. Such fastening zones have novel configurations that are especially suited for absorbent articles comprising outer covers or reusable outer covers that are configured to be engaged with disposable absorbent inserts, although the present disclosure is not limited to such. In particular embodiments, the absorbent articles may be pants that are configured to be pulled-up over the legs and the hips into position on the wearer. In some instances, pants are donned while the user is in a standing, or partially standing, position. As such, fastening zones are provided to enable easy joining, separation, and/or readjusting of the front and rear waist regions while the wearer is in the standing position or when the pants are being pulled up over the legs, hips, and buttocks. Example details of the outer cover or reusable outer cover and the disposable absorbent inserts will first be described briefly to provide context to the fastening zone disclosure. The present disclosure, however, is not limited to two-piece wearable absorbent articles as described herein, but also covers any suitable absorbent articles, namely disposable diapers (taped and pants) and adult incontinence articles, that can benefit from the fastening zone configurations of the present disclosure.

Two-Piece Wearable Absorbent Articles

In an embodiment, FIG. 1A depicts an example of a wearable absorbent article 10 that is a pant positioned about a lower torso of a wearer. The pant comprises an outer cover 20 having a front waist edge 21, a rear waist edge 22, leg opening edges 23, fastening ears 29, and leg bands. The outer cover comprises an inner, wearer-facing surface 25 (not illustrated in FIG. 1A) and outer, garment-facing surface 24. The outer cover 20 may be configured to receive an insert as discussed in further detail below. The fastening ears 29 may be used to permanently or refastenably join the rear waist region to the front waist region or vice versa to form the pant. In an embodiment, one of the fastening ears 29 may be permanently joined to the front waist region, while the other fastening ear 29 may be releasably joined to the front waist region. In an embodiment, the fastening ears 29 may be positioned on the front waist region and be permanently or refastenably joined to the rear waist region to form the pant. The pant may also comprise a pouch-like structure 75 in a crotch region thereof.

Figure 1B:
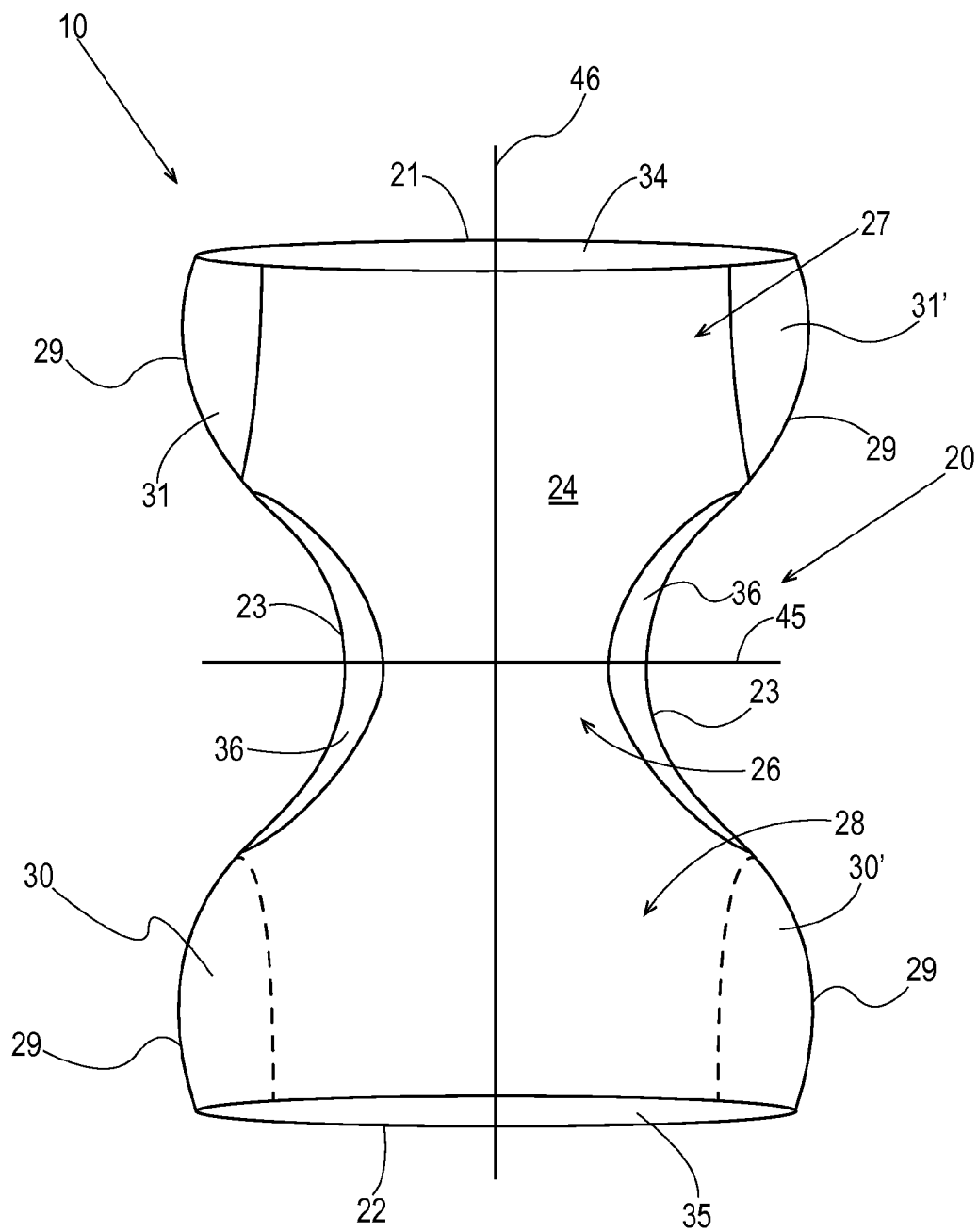
FIG. 1B is a plan view of an outer cover of FIG. 1A opened and laid flat, outer surface facing (i.e., garment-facing surface) the viewer in accordance with a non-limiting embodiment of the present disclosure.

FIG. 1B illustrates the outer cover 20 of the pant as it may appear open and laid flat. In FIG. 1B, the outer surface 24 faces the viewer. The outer cover 20 may comprise a front waist region 27, a crotch region 26, and a rear waist region 28. The front waist region 27 may be positioned on a first side of a lateral axis 45 and the rear waist region 28 may be positioned on a second side of the lateral axis 45. The crotch region 26 may extend across the lateral axis 45 such that a portion of the crotch region 26 is positioned on a first side of the lateral axis and a second portion of the crotch region 26 is positioned on a second side of the lateral axis. The outer cover 20 may comprise a front waist band 34, a rear waist band 35, and a longitudinal axis 46. FIG. 1C illustrates an outer cover 20 with an insert 50 positioned therein and attached thereto. In FIG. 1C the fastening ears 29 have been joined. FIG. 1D illustrates the outer cover 20 of FIG. 1C without the insert 50 and with the fastening ears 29 unjoined.

FIG. 1E is an illustration of a top view of a pant having fastening zones positioned on the side of the pant. FIG. 1F is an illustration of a top view of a pant having fastening zones positioned toward the front of the pant. FIG. 1G is an illustration of a top view of a pant having fastening zone positioned toward the rear of the pant. It will be understood that each embodiment disclosed herein may have fastening zones or seams at the side, in the front, or in the rear of the pant, although not specifically illustrated for each particular embodiment.

Any of the fastening zones of the present disclosure may create overlap seams (FIG. 1H) or butt seams (FIG. 1I). Other seams known to those of skill in the art may also be provided.

Figure 2A:
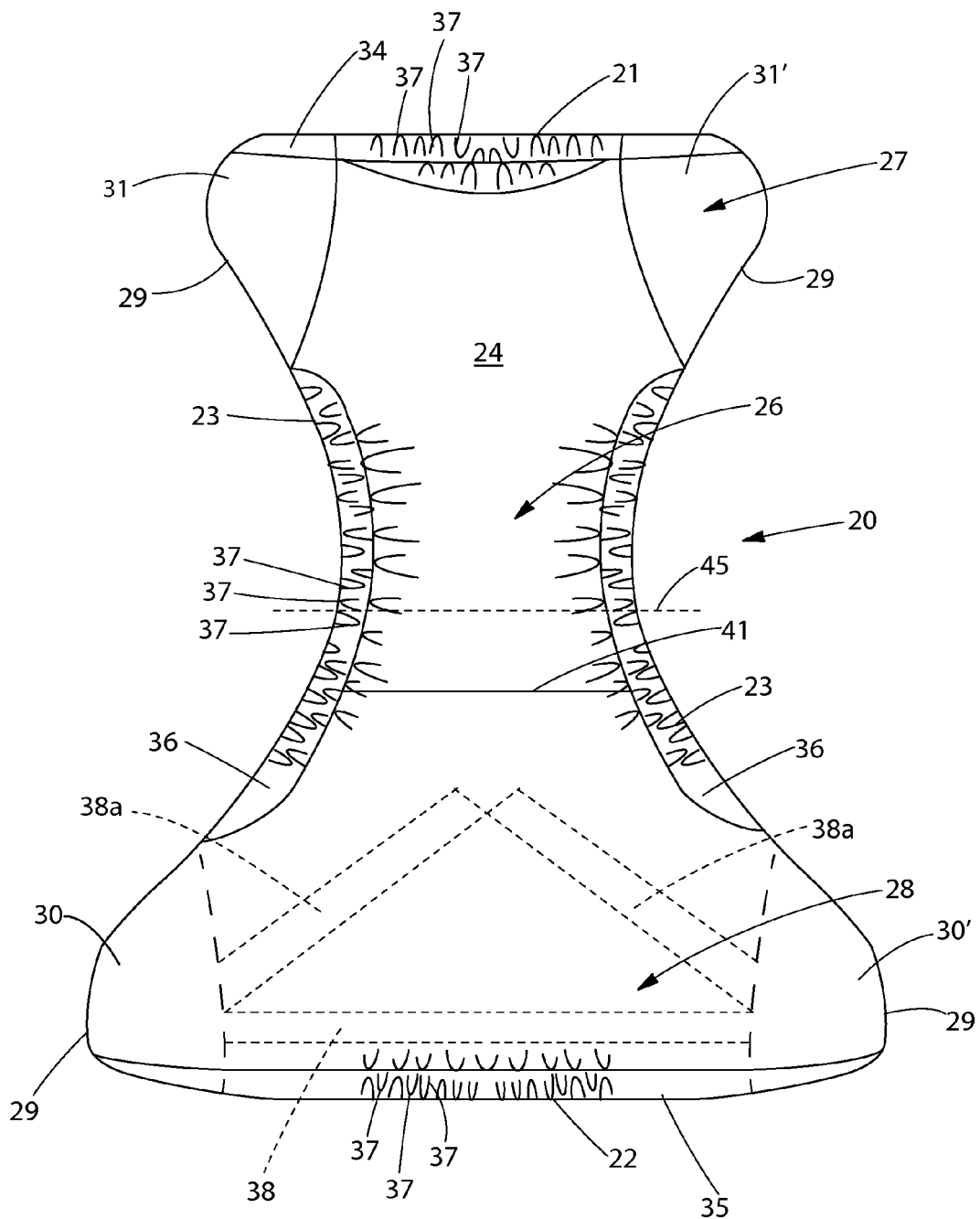
FIG. 2A is a plan view of an outer cover opened and laid flat, outer surface facing the viewer in accordance with a non-limiting embodiment of the present disclosure.
Figure 2B:
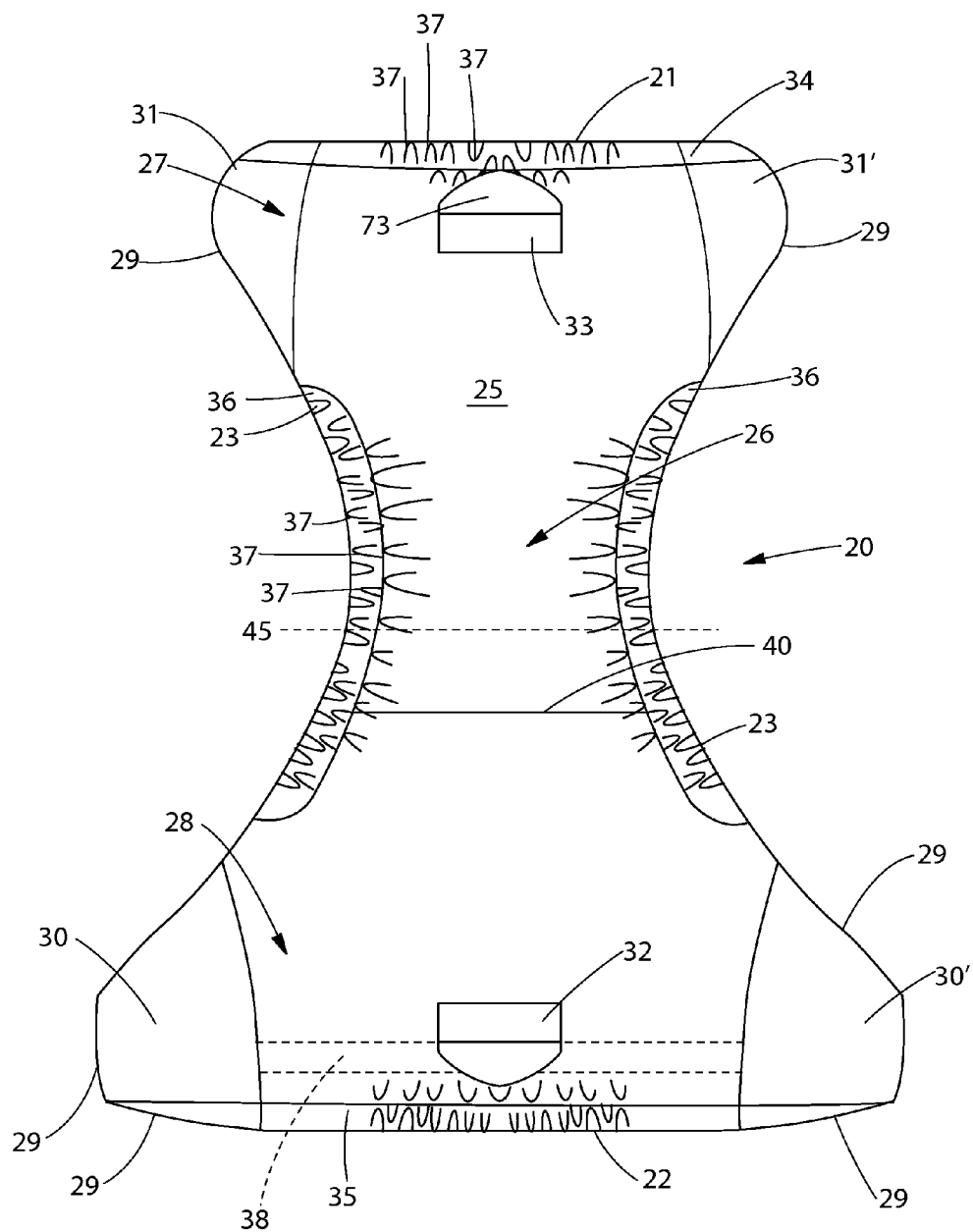
FIG. 2B is a plan view of an outer cover opened and laid flat, inner surface (i.e., wearer-facing surface) facing the viewer in accordance with a non-limiting embodiment of the present disclosure.
Figure 2C:
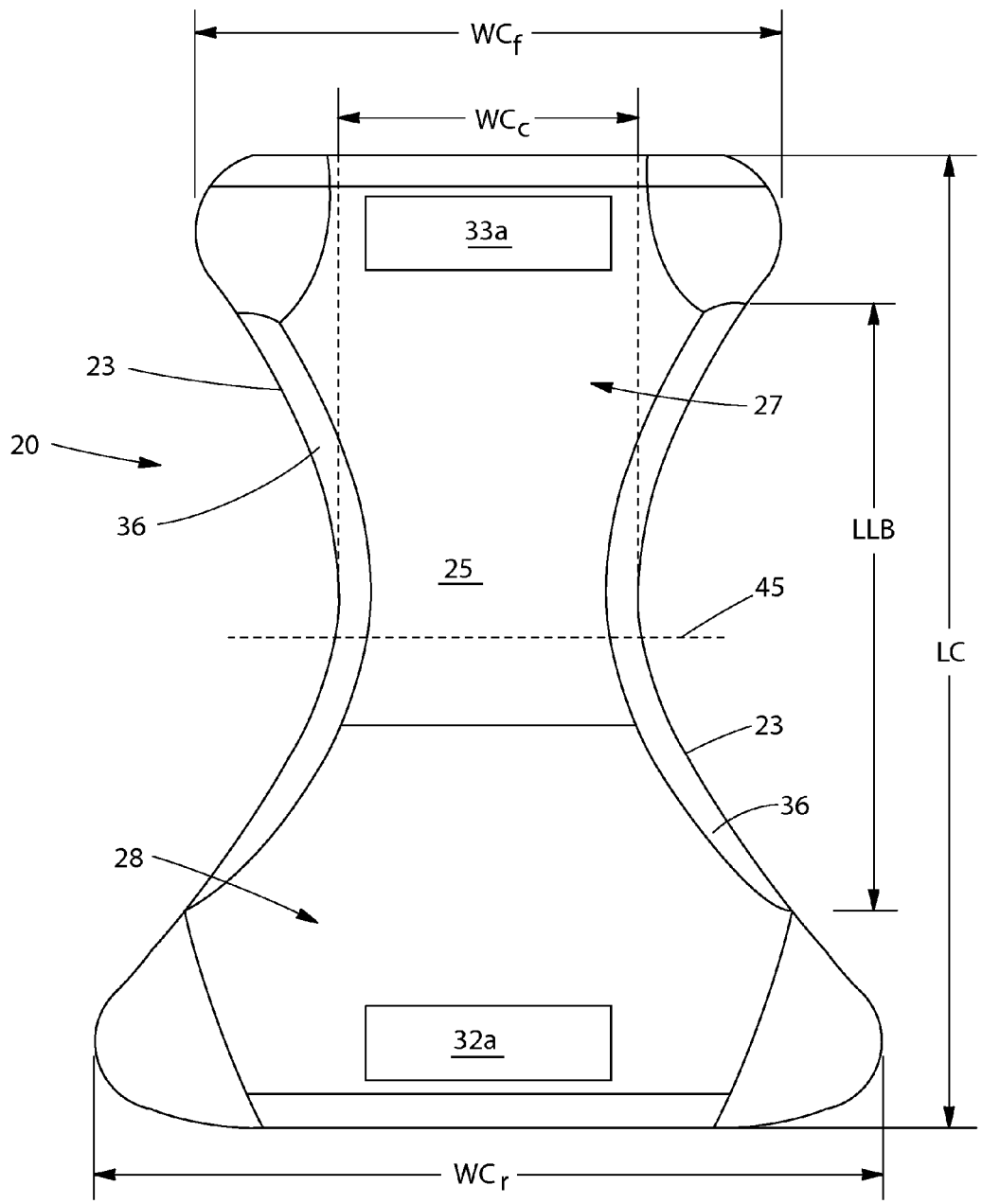
FIG. 2C is a plan view of an outer cover opened and laid flat, inner surface facing the viewer in accordance with a non-limiting embodiment of the present disclosure.

In some embodiments, FIGS. 2A, 2B and 2C depict an outer cover 20 of the present disclosure as it may appear opened and laid flat. In FIG. 2A, the outer, garment-facing surface of outer cover 20 face the viewer, while in FIGS. 2B and 2C, the inner, wearer-facing surfaces of outer cover 20 face the viewer. The front and rear waist edges 21, 22 are depicted at the top and bottom of the drawings, respectively. The outer covers 20 may have a crotch region 26, a front waist region 27, a rear waist region 28, and pairs of fastening ears 29 laterally extending from the rear waist region 28 and the front waist region 27. Each of the fastening ears 29 may comprise a side of a fastening zone (31 and 30 when joined together form a fastening zone and 31' and 30' when joined together form a fastening zone). The fastening zone 31 and 30 or first fastening zone and the fastening zone 31' and 30' or second fastening may be may be engaged with each other to join the front waist region 27 to the rear waist region 28. The first fastening zone is on a first second of the longitudinal axis and the second fastening zone is on a second side of the longitudinal axis.

Referring to FIG. 2C, the outer cover 20 may have a length LC from the forwardmost portion of the front waist edge 21 to the rearwardmost portion of the rear waist edge 22, and an outer cover lateral axis 45 equally dividing this length. Thus, the front waist region 27 may be positioned on a first side of the outer cover lateral axis 45 and the rear waist region 28 may be positioned on a second side of the outer cover lateral axis 45. The crotch region 26 may be positioned on the first side of the outer cover lateral axis 45 and on the second side of the outer cover lateral axis 45. The outer cover 20 may have disposed thereon one or more attachment zones such as front and rear attachment zones 33, 33a and 32, 32a for attachment of an insert to the outer cover 20. Other configurations of front and rear attachment zones are also contemplated although not illustrated in the figures for brevity.

Figure 3:
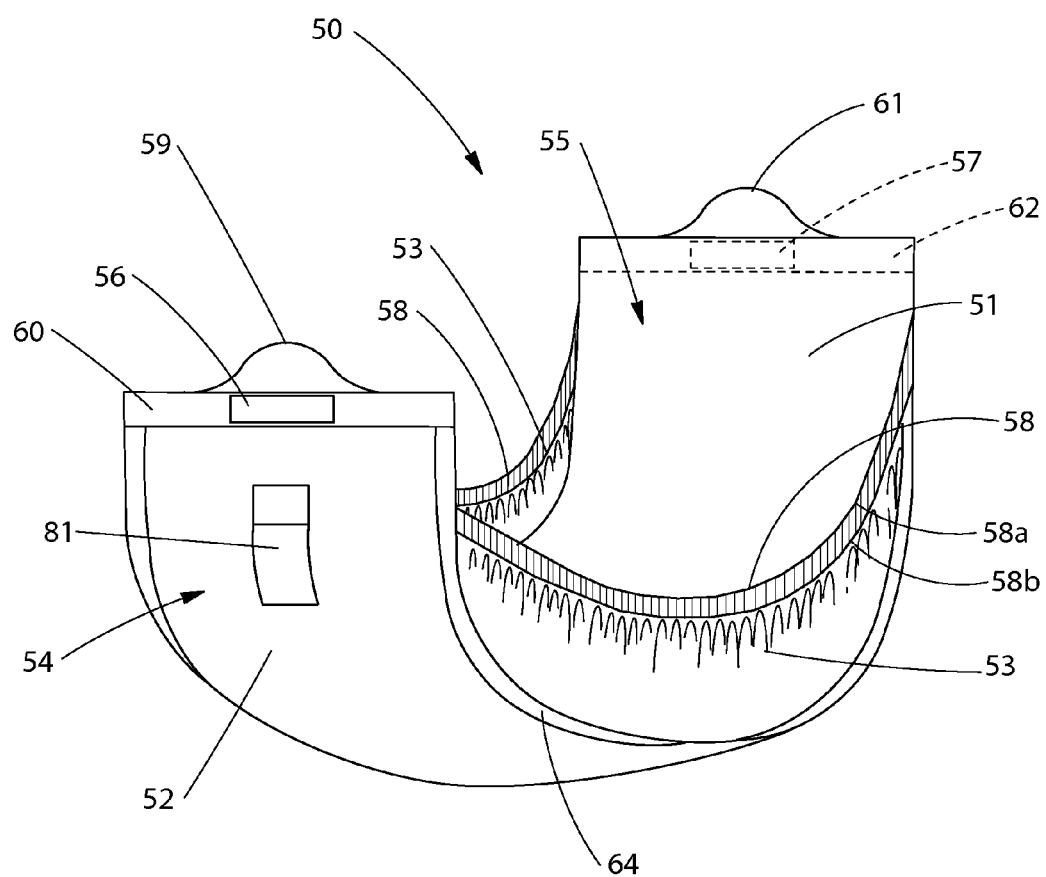
FIG. 3 is a perspective view of an insert shown apart from an outer cover, as it might appear in a free-standing, relaxed state in accordance with a non-limiting embodiment of the present disclosure.
Figure 4:
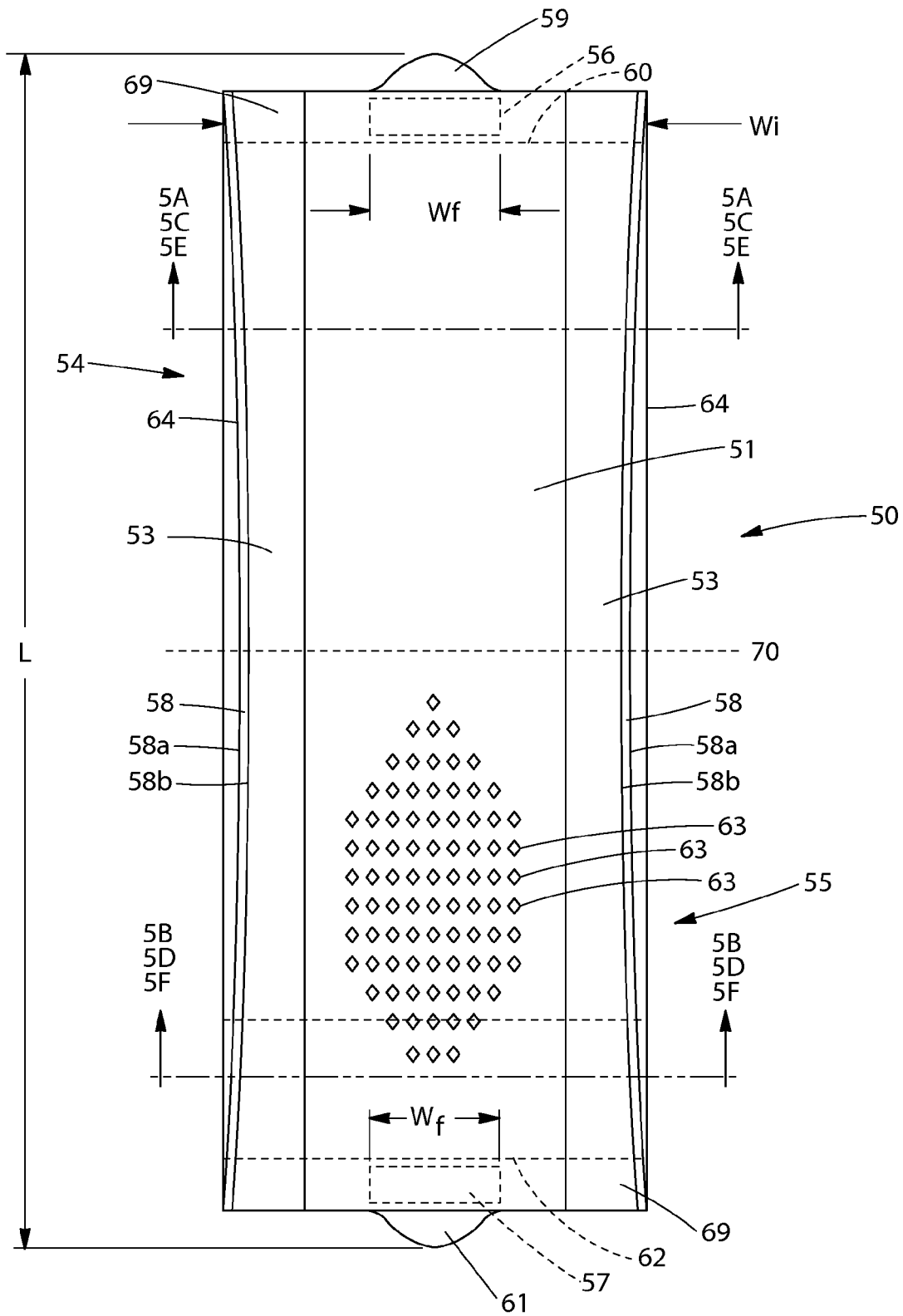
FIG. 4 is a plan view of an insert shown stretched out and laid flat, inner surface facing the viewer in accordance with a non-limiting embodiment of the present disclosure.

FIG. 3 depicts a disposable absorbent insert 50 that may form an inner component of the wearable absorbent article 10, shown in perspective view as it might appear in a free-standing, relaxed state, apart from the outer cover 20. The insert 50 may be designed to contain and/or absorb body exudates, and may be made of pliable materials as will be described further below. The insert 10 may have forward region 54 and rearward region 55, and may include one or more front fastener components 56 and one or more rear fastener components 57 configured to engage the front and rear attachment zones 33 and 32 on the outer cover 20. The insert 10 may include a body-facing liner or topsheet 51, an outer liner or backsheet 52, and a pair of standing cuffs 53. Referring to FIG. 4, the insert 50, when fully opened and laid flat, may have a length L from the forwardmost portion of the forward region 54 to the rearwardmost portion of the rearward region 55, and an insert lateral axis 70 equally dividing this length. Thus, the forward region 54 is positioned on a first side of the insert lateral axis 70 and rearward region 55 may be positioned on a second side of the insert lateral axis 70.

In an embodiment, referring to FIGS. 2B and 3, the insert 50 may have rear fastener component 57 disposed thereon. Alternatively, or in addition, the outer cover 20 may have rear insert fastener component 32 disposed thereon. Similarly, the insert 50 may have front fastener component 56 disposed thereon. Alternatively, or in addition, the outer cover 20 may have front insert fastener component 33 disposed thereon. If a two-component fastening system is used, fastener component pairs 57, 32 and 56, 33 may be cooperating components that affect fastening therebetween when these respective components are brought together. Thus, in the example depicted, in order to install the absorbent insert 50 into the outer cover 20, a user may lay the outer cover 20 flat, inner surface 25 facing up, stretch and orient the insert 50 such that the rear fastener component 57 faces the rear insert fastener component 32 and the front fastener component 56 faces the front insert fastener component 33, and bring these respective fastener component pairs 57, 32 and 56, 33 together to effect fastening therebetween. In other embodiments, the user may position the insert 50 into a closed waist circumference pant, by folding the insert about the lateral axis 46, inserting the insert 50 into and at least partially through the closed waist circumference of the outer cover 20, and bringing the respective fastener component pairs 57,32, and 56, 33 together.

If it is desired that the outer cover 20 be reusable, for the outer cover 20 to remain substantially sanitary and useful (without requiring laundering or disposal) after removal and replacement of an insert, it may be desired that all parts of the outer cover 20 remain substantially unsoiled after an exudation of waste (especially fecal matter) by the wearer. Thus, it may be desired that when the insert 50 is installed within an outer cover 20, there is no non-removable portion or component of the outer cover 20 that lies over or covers a substantial portion of wearer-facing surfaces of the insert 50. Stated another way, no non-removable portion or component of the outer cover 20 is situated between a substantial portion of the insert 50 and the wearer when the wearable absorbent article 10 is worn, at least in the areas proximate to wearer body features that discharge exudates. Thus, it may be desired that the outer cover 20 include no non-removable cover sheet or the like that covers or contains substantial portions of wearer-facing surfaces of the insert 50 within the outer cover 20, nor any overlying structures such as pockets, straps or flaps that substantially wrap or cover the insert proximate to exudate discharge points, or lie substantially between the insert 50 and the wearer's anus and/or genitals, when the wearable absorbent article 10 is worn. If the outer cover 20 lacks such overlying structures, this may increase the likelihood that the wearer's exudates will contact only the insert 50, and not portions of the outer cover 20.

Referring to FIGS. 1A, 2A and 2B, it can be seen that the wearable absorbent article 10 may be placed on a wearer by attaching the insert 50 to the outer cover 20, attaching the fastening zones 30 and 31 and 30' and 31 to form a pant, and pulling the pant up the legs and over the thighs, hips, and buttock into the position illustrated in FIG. 1A. In an embodiment, the outer cover 20 may come from a manufacturer in a pre-formed state (i.e., continuous waist and leg perimeters) having permanent or refastenable seams, for example. In such an instance, the insert 50 may be inserted into the outer cover 20 and then pulled up the legs, over the thighs, hips, and buttocks into position on a wearer. When the insert 50 has been installed into the outer cover 20, the insert 50 may then be disposed within the outer cover 20, next to the wearer, with the standing cuffs 53 oriented and extending longitudinally adjacent the inner portions of leg edges 23 (i.e., longitudinally between the wearer's legs).

Materials

The outer cover 20 and/or layers or portions thereof may be made of any knitted, woven or nonwoven textile, film, or textile-like material that is appropriately compatible with skin of the intended wearer(s). The outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in co-pending U.S. Patent Application Publication Nos. 2010/0179495, 2010/0179503, and 2011/0172628, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on Jan. 14, 2010. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the U.S. applications identified immediately above. Thus, the outer cover 20 may be constructed of materials and construction that make it reusable and/or washable.

The durable materials of which the outer cover 20 may be constructed may include any natural or synthetic textile materials known in the diaper, pant, underwear, performance clothing, sport clothing, or general clothing or textile arts. The durable materials may include woven or knitted textiles made of natural fibers such as cotton, linen, wool, bamboo, hemp, silk, and/or rayon, for example, as well as blends of any of these fibers with any other(s), or with synthetic fibers. Examples of synthetic fibers suitable for use as components of the durable materials include polyester, nylon, spandex and/or other elastomer fibers.

Semi-durable outer cover materials may include any natural or synthetic nonwoven web and/or film materials known in the diaper or pant arts. Semi-durable materials of which the outer cover 20 may be constructed may include non-woven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of the outer cover 20.

The outer cover 20 also, or additionally, may include a laminated or substantially separate film layer, which may be elastic, to provide enhanced liquid penetration resistance and/or elastic properties.

The outer cover 20 may be formed of a single layer of a durable or semi-durable material, or may have two or more layers in the front waist region 27, the rear waist region 28, the crotch region 26, and the leg openings. Accordingly, referring to FIG. 2B, an example inner surface 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming the inner surface 25 to more readily absorb liquid, or transmit liquid therethrough. This may serve to provide supplemental absorbency within the outer cover for an event in which liquid exudates escape the insert 50, reducing the likelihood that the outer cover 20 will leak. Alternatively, it may provide one way of communicating to the user that liquid exudates have escaped the insert 50, by causing wetness to be transmitted through to the outer cover outer layer such that wetness is visible on outer surface 24. Alternatively, it may serve to provide a layer that tends to draw moisture away from the skin, for a drier, more comfortable feel.

Referring again to FIGS. 2A and 2B, in addition to forming differing layers of differing materials, it may be desirable to form a single layer of differing materials, for example, differing materials in the respective front, crotch, and/or rear regions 27, 26, and 28 of the outer cover 20. Such differing materials may be joined at a seam such as an inner seam 40 (FIG. 2B) and/or outer seam 41 (FIG. 2A). In other embodiments, the two different properties may be inherent to a single piece of fabric, for example.

Elasticized Waistbands, Leg Bands

Referring again to FIGS. 1A, 2A and 2B, a front waist band portion 34, a rear waist band portion 35, and leg band portions 36 are illustrated. One or more of these band portions 34, 35, 36 may be formed of one or more strands or strips including an elastomeric material, such as spandex or a blend of spandex and other fibers, enveloped by a nonwoven or textile material, which may include the edges of the material forming the inner and/or outer layers of outer cover 20, to form and elasticize the respective band portions. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portions may be disposed along the edge of the outer cover, and in some circumstances it may be desired to have the band portions situated along substantially the entire length of the leg and/or front or rear waist openings so as to form bands that substantially or completely encircle the wearer's legs and/or waist while outer cover 20 is worn. The gathered material within the ruffles 37 may serve to accommodate stretching of the waist band portions 34, 35 and the leg band portions 36.

Anchoring Bands

In an embodiment, the outer cover 20 also may include an anchoring supplement, such as anchoring band 38, disposed on or in the outer cover rear waist region 28 as indicated in FIGS. 2A, 2B. Various anchoring bands may also extend into and/or through the crotch region 26 and/or the waist regions 27 and 28. In an embodiment, one anchoring band may cross over another anchoring band. As suggested in FIGS. 2A and 2B, the anchoring band 38 may be affixed along a layer, or disposed between layers, forming the inner surface 25 and the outer surface 24 of the outer cover 20. The anchoring band 38 may include an elastomeric or elasticized strip or band of material, affixed to the outer cover 20 at locations proximate to its rearward corners or proximate to fastening ears 29. When strained laterally by application to the wearer, the anchoring band 38 may serve to provide, or supplement, lateral tensile forces in the wearable absorbent article 10 about the wearer's waist, thereby tending to draw the waist opening snug, enhancing fit and enhancing securement of the wearable absorbent article 10 about the wearer's waist. The elastic property (e.g., elastic modulus and maximum elastic extension) of the anchoring band 38 may be higher than or different than the elastic property of the surrounding, adjacent, or coextensive outer cover materials.

In another example, instead of, or in addition to, being oriented substantially laterally as suggested by the depicted location of the anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover 20 and/or the fastening ears 29, and respectively extend toward both the lateral and longitudinal center of the outer cover 20, as suggested in FIG. 2A.

Outer Cover Asymmetry

In order to enhance and/or maximize fit, wearer comfort and appearance of the outer cover 20, it may be desirable to fashion the outer cover 20 so as to accommodate anatomical contours and body movements of the intended wearer. For example, as suggested by FIGS. 2A and 2B, the outer cover 20 may have differing shape and/or greater material surface area in the rear waist region 28 than in the front waist region 27. Human anatomy in the lower torso/hip/thigh region is asymmetric about the lateral plane of the body, i.e., the geometry of the front of the human body is different than that of the back. To provide for better fit and comfort, the outer cover geometry and functionality, including stretch properties, may be adapted accordingly. Differing shape and/or greater material surface area in the rear waist region 28 may serve to better cover the buttocks through movements of the wearer (including sitting and/or bending forward at the hips), while lesser material surface area in the front waist region 27 may serve to avoid material bunching and/or an ill-fitting appearance, particularly when the wearer is in positions including sitting and/or bending forward at the hips. As a result, the outer cover 20 may be asymmetric in shape or surface area across the outer cover lateral axis 45.

For purposes of this description, when used with respect to an outer cover 20, "asymmetric" and "asymmetry" mean that features, geometry (e.g., shape), materials and/or construction on one side of the outer cover lateral axis 45 differ substantially in some respect from those on the other side of the outer cover lateral axis 45. Such asymmetric construction results from having various features of the outer cover 20 designed to accommodate the body features and functions of the intended wearer as they differ front-to-rear, to enhance containment/absorbency performance, comfort, fit and/or appearance of the wearable absorbent article, and/or to economize on use of materials. "Asymmetric" and "asymmetry" do not refer to differences across the outer cover lateral axis 45 that are attributable to features that may be included on an outer cover 20 only for purposes of: purely cosmetic coloration or surface decoration; fastening an insert (such as fastening zones described herein); bundling, folding, storing or carrying the outer cover; indicia for orienting an insert within an outer cover 20 or vice versa (such as orientation indicia described herein), or for other purposes substantially unrelated to the body features and functions of the intended wearer as they differ front-to-rear, to affect performance, comfort, fit, and/or physical appearance of the wearable absorbent article 10, and/or to economize on use of materials.

Examples of Possible Absorbent Insert Details

Examples of features of an absorbent insert 50 will be described with reference to FIGS. 3, 4, and 5A-F. The present disclosure also contemplates the use of other inserts with other features and is not limited to the inserts described below.

As noted above, FIG. 3 depicts a disposable absorbent insert 50 that may form an inner component of a wearable absorbent article 10 as described herein, shown in perspective view as it might appear in a free-standing, relaxed state, apart from an outer cover 20. FIG. 4 depicts an example of an absorbent insert 50 shown stretched out and laid flat (against elastic-induced contraction to a position similar to that shown in FIG. 3), wearer-facing surfaces facing the viewer. FIGS. 5A-5F depict cross sectional views of an insert 50 as indicated in FIG. 4, in various possible examples.

The insert 50 may have a topsheet 51 and a backsheet 52 forming an envelope-like enclosure for absorbent core materials such as those described further below. The topsheet 51 and the backsheet 52 may be affixed together along longitudinal seams 64, and along lateral seams 69. The insert 50 also may have longitudinal standing cuffs 53 affixed therealong.

Topsheet

The topsheet 51 may be formed of a liquid-permeable nonwoven web material. It may be desired that the material forming the topsheet 51 is compliant, soft-feeling, and non-irritating to the wearer's skin. It may be desired that at least a portion of the topsheet 51 may be liquid pervious, permitting liquids to readily penetrate through its thickness. A suitable topsheet may be manufactured from a wide range of materials, such as porous foams, reticulated foams, apertured plastic films, apertured nonwoven materials, or woven or nonwoven materials of natural fibers (e.g., wood or cotton fibers), synthetic fibers (e.g., polyester or polypropylene fibers), or a combination of natural and synthetic fibers. If the topsheet 51 includes fibers, the fibers may be spunbond, carded, wet-laid, meltblown, hydroentangled, or otherwise processed as is known to those of skill in the art. Any suitable topsheets known to those of skill in the art may be used with the inserts of the present disclosure.

Backsheet

The backsheet 52 is generally that outer liner portion of the insert 50 forming the garment-facing surface thereof, and prevents, or at least inhibits, the exudates absorbed and contained within the insert 50 from wicking through and soiling the outer cover 20. In some circumstances it may be desired that the backsheet 52 is substantially impervious to liquids. Any suitable backsheets known to those of skill in the art may be used with the inserts of the present disclosure.

Absorbent Core

In an embodiment, referring to FIGS. 5A-F, the insert 50 may have an absorbent core 71 within the envelope-like structure formed by the topsheet 51 and the backsheet 52. The absorbent core 71 may comprise any absorbent material which is generally compressible, conformable, non-irritating to the wearer's skin, and capable of absorbing and retaining liquids, such as urine and other certain body exudates. The absorbent core 71 may comprise a wide variety of liquid-absorbent materials commonly used in disposable diapers and other absorbent articles such as comminuted wood pulp, which is generally referred to as airfelt and/or superabsorbent polymers.

The absorbent core 71 may include liquid acquisition/distribution material 65, and storage material 66. Generally, acquisition/distribution material 65 may have comparatively rapid absorption and wicking properties, but also may have limited absorption capacity. Conversely, generally, the storage material 66 may have comparatively slower absorption and wicking properties, but also may have greater absorption capacity. Thus, the acquisition/distribution material 65 may serve to rapidly absorb and distribute gushes of liquid such as urine, while the storage material 66, having greater absorption capacity, may serve to absorb such liquid from the acquisition/distribution material and store it for the time needed until the insert 50 may be replaced.

Standing Cuffs

The insert 50 also may have a pair of longitudinal standing cuffs 53 attached partially or entirely along the longitudinal length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and U.S. Published Application No. 2007/0239130 and U.S. Pat. No. 8,002,760. As shown in FIG. 3, the standing cuffs 53 may have one or more strands or strips of cuff elastics 58a, 58b disposed longitudinally therealong. If such cuff elastics 58a, 58b are pre-strained prior to being affixed to the web material forming the standing cuffs 53, resulting longitudinal tensile forces therealong may cause the web material forming the standing cuffs 53 to gather as shown, and cause the cuffs 53 to extend from the body of the insert 50 (upwardly relative to FIG. 3), or causing them to "stand". This feature causes the standing cuffs 53 to form a gasketing structure along the wearer's body when the wearable absorbent article 10 including the insert 50 is worn, longitudinally on either side of the anatomical features where waste is exuded. Thus, the standing cuffs 53 may serve to enhance the exudate containment capability of the insert 50 and, and as a result, of the wearable absorbent article 10. As with the backsheet 52, the standing cuffs 53 may be formed of a substantially liquid impermeable web so as to contain and isolate liquid exudates from the outer cover 20, outer clothing and environment of the wearer. At the same time, the standing cuffs 53 may be vapor permeable to provide for breathability of the insert 50 and the wearable absorbent article 10, reducing humidity in the areas between the insert and the wearer's body, and helping reduce the likelihood of skin irritation and/or rashes that may result from over-hydration of the skin. In another example, the material forming the standing cuffs 53 may be integral with the material forming the backsheet 52, such as described in, by way of non-limiting example, U.S. Published Patent Application. No. 2007/0239130.

Insert Asymmetry

Referring to FIG. 4, the insert 50 may have an insert lateral axis 70 that equally divides its longitudinal length. The insert 50 may have a structure that is asymmetric across the insert lateral axis 70. For purposes of this description, with used with respect to an insert, "asymmetric" and "asymmetry" mean that features, geometry (e.g., shape), materials and/or construction on one side of the insert lateral axis 70 differ substantially in some respect from those on the other side of the insert lateral axis 70. Such asymmetric construction results from having various features of the insert 50 designed to accommodate the body features and functions of the intended wearer (i.e., body contours, excretory and eliminatory functions) as they differ front-to-rear, to enhance containment/absorbency performance, comfort, fit and/or appearance of the wearable absorbent article 10, to economize on use of materials and/or to reduce volume of disposable waste. "Asymmetric" and "asymmetry" do not refer to differences across the insert lateral axis 70 that are attributable to features that may be included on an insert only for purposes of: purely cosmetic coloration or surface decoration; fastening to an outer cover (such as fastener components described herein); user grasping of the insert (such as a grasping structure described herein); as indicia for orienting an insert within an outer cover (such as orientation indicia described herein); or for other purposes substantially unrelated to the body features and functions of the intended wearer as they differ front-to-rear, to affect performance, comfort, fit and/or physical appearance of the wearable absorbent article 10, to economize on use of materials and/or to reduce volume of disposable waste.

As one example, the topsheet 51 may one or more have apertures 63 therethrough, predominately in the crotch and/or the rearward region 55 as suggested in FIG. 4. The apertures 63 may permit liquid or low viscosity fecal material to penetrate the topsheet 51 and reach absorbent materials in the absorbent core 71 more rapidly than would occur without such apertures, enhancing liquid feces absorption and containment capability of the insert 50.

In an embodiment, all or a portion of the rearward region 55 of insert 50 may include acquisition/distribution material 65 but less or no storage material 66 as compared with the forward region 54, as may be seen by comparison of FIGS. 5A and 5B, 5C and 5D, and 5E and 5F, respectively. By this particular absorbent core asymmetry, the storage material 66 may be located predominately in the front of the wearable absorbent article 10 when worn. This may provide a predominate proportion of the insert's urine storage capacity closer to the urine exudation point of the wearer to reduce the likelihood of leakage, and remove potentially uncomfortable and/or unsightly size and bulk from between the wearer's legs or the wearer's backside area, particularly relevant when the storage material 66 becomes swollen with absorbed liquid. Additionally, this particular asymmetry provides for economization of the amount of the storage material 66 used, by locating it in only a portion of the insert 50 rather than substantially along the entire insert 50. The liquid storage capacity of the forward region of the absorbent core 71 may be greater than that of the rearward region of the absorbent core 71 as measured by the Teabag Centrifuge Capacity test disclosed in U.S. Pat. No. 6,278,037.

Figure 5A:
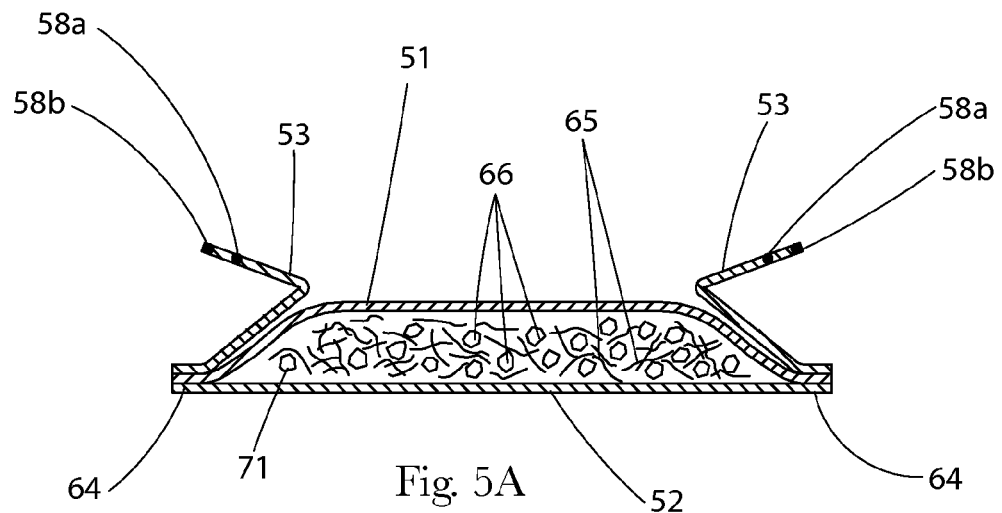
FIG. 5A is a cross-sectional view of an example of an insert such as shown in FIG. 4, taken at line 5A-5A of FIG. 4 in accordance with a non-limiting embodiment of the present disclosure.
Figure 5B:
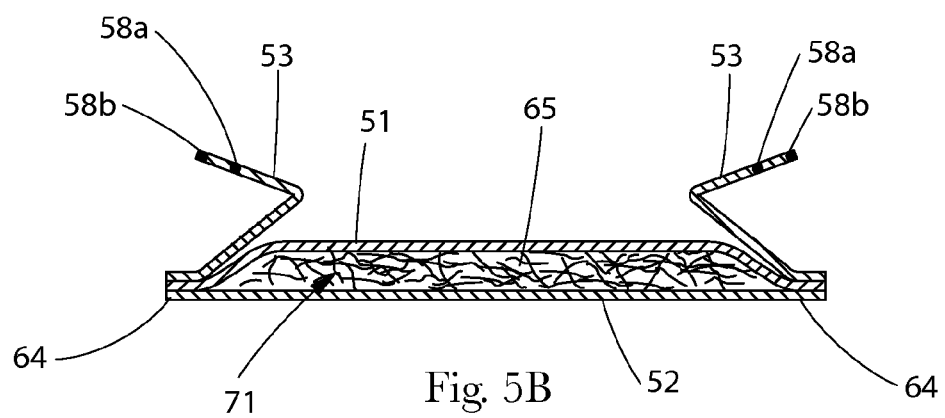
FIG. 5B is a cross-sectional view of an example of an insert such as shown in FIG. 4, taken along line 5B-5B of FIG. 4 in accordance with a non-limiting embodiment of the present disclosure.
Figure 5C:
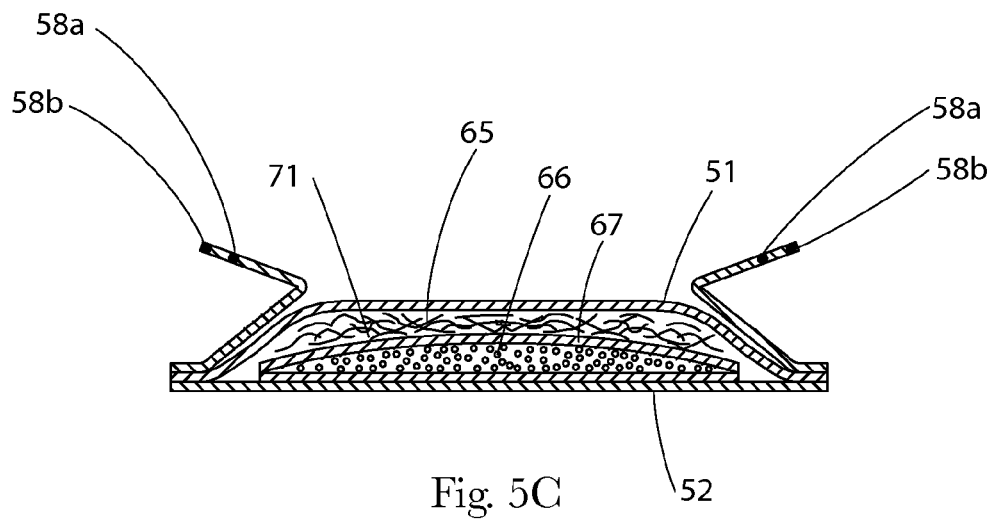
FIG. 5C is a cross-sectional view of another example of an insert such as shown in FIG. 4, taken along line 5C-5C of FIG. 4 in accordance with a non-limiting embodiment of the present disclosure.
Figure 5D:
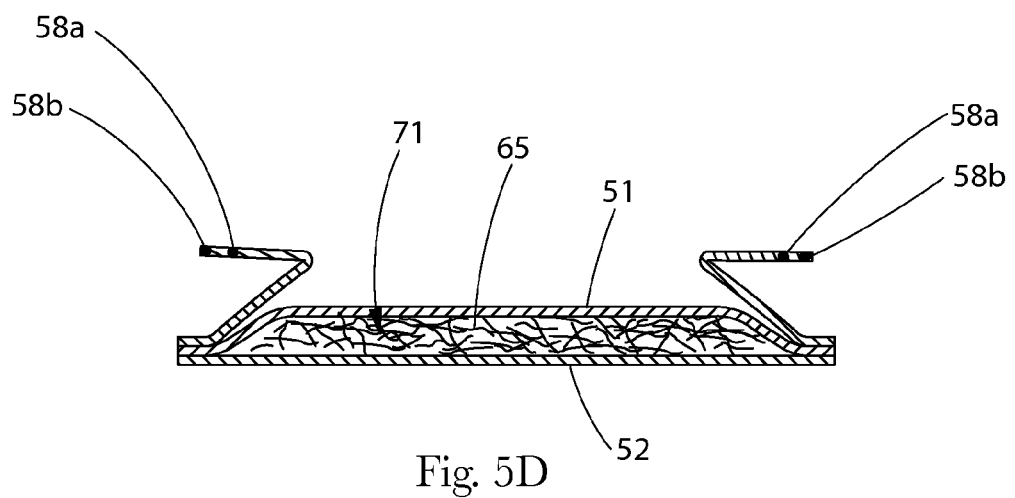
FIG. 5D is a cross-sectional view of another example of an insert such as shown in FIG. 4, taken along line 5D-5D of FIG. 4 in accordance with a non-limiting embodiment of the present disclosure.
Figure 5E:
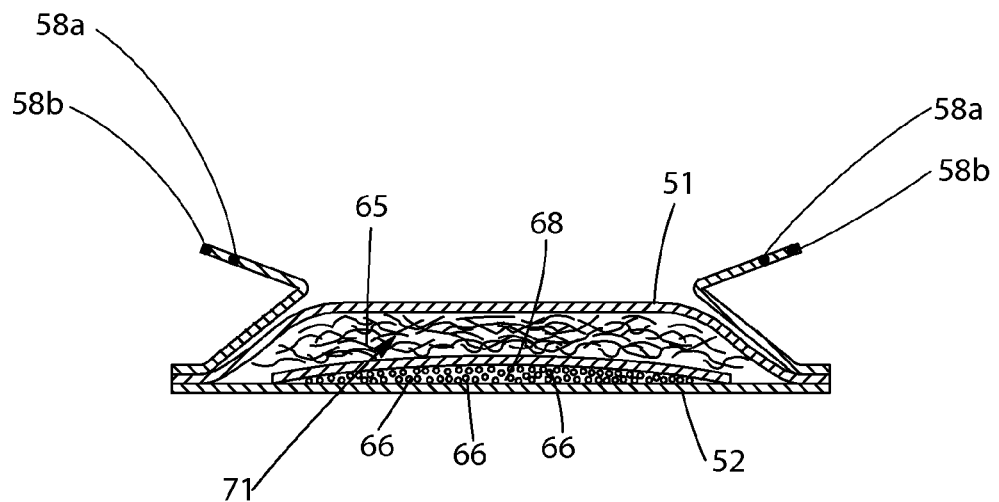
FIG. 5E is a cross-sectional view of another example of an insert such as shown in FIG. 4, taken along line 5E-5E of FIG. 4 in accordance with a non-limiting embodiment of the present disclosure.
Figure 5F:
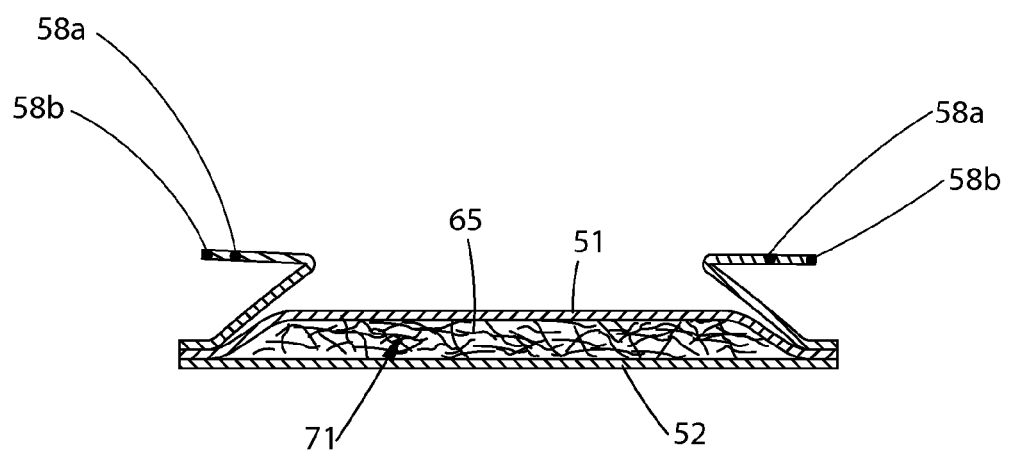
FIG. 5F is a cross-sectional view of another example of an insert such as shown in FIG. 4, taken along line 5F-5F of FIG. 4 in accordance with a non-limiting embodiment of the present disclosure.

Referring to FIGS. 5A, 5C and 5E, in other examples, the absorbent material 66 in the forward region 54 may be, respectively, dispersed within the acquisition/distribution material 65 (FIG. 5A), contained within a separate liquid permeable structure or envelope 67 in fluid communication with the acquisition/distribution material 65 (FIG. 5C); or dispersed on, or within an adherent matrix of, retaining material 68, and in fluid communication with the acquisition/distribution material 65 (FIG. 5E). Conversely, the rearward region 55 may predominately contain the acquisition/distribution material 65, but less storage material 66 as compared with the forward region 54, or none (FIGS. 5B, 5D, 5F). Materials in the forward region 54 also may be disposed according to construction described in one or more of U.S. Patent Application Publication Nos. 2008/0312617, 2008/0312618, 2008/0312628, 2008/0312619, 2008/0312620, 2008/0312621, 2008/0312622, 2008/0312625, 2008/0312624, and U.S. Pat. No. 8,017,827, with a differing construction in the rearward region 55.

In another example, the storage material 66 and the acquisition/distribution material 65 may occupying differing, distinct layers of the absorbent core 71, as suggested by FIG. 5C.

In the event of a pant, the insert may be symmetric across the insert lateral axis 70.

Grasp Structures, Removal and Disposal Aids

Referring to FIGS. 3, and 4, the insert 50 also may include respective user grasp structures 59, 61. The user grasp structures 59, 61 may be provided to enable the user to quickly and easily grasp the insert 50 proximate its respective ends.

Grasp structures as shown and/or suggested may enable the user to more quickly grasp and stretch the insert 50 from a contracted position similar to that depicted in FIG. 3, to an extended position similar to that depicted in FIG. 4, which may be desirable for installing the insert 50 into an outer cover 20.

The user grasp structures 59, 61 may include tab-like extensions as shown in FIGS. 3 and 4, with free ends unattached to the outer cover 20 when the insert 50 is installed therein, which are easily graspable. The user grasp structures 59, 61 may have different forms as well. By way of non-limiting example, user grasp structures may take the form of loop-like extensions extending from the ends of the insert 50, finger holes through the insert 50 proximate the ends thereof, pockets with openings facing the lateral centerline 70 of the insert 50, and other structures that facilitate grasping and pulling of the insert 50 at locations proximate to its ends.

Referring again to FIG. 3, an insert 50 may also include a disposal aid 81, configured to hold the insert 50 in a folded or rolled configuration for convenience of neat handling and disposal following removal of the soiled insert 50 from an outer cover 20. As suggested in FIG. 3, the disposal aid 81 may be in the form of a strip of removable/refastenable tape. Other forms of disposal aids, which serve to hold an insert 50 in a folded or rolled up condition with the topsheet 51 in and the backsheet 52 out, may be used.

Types, Locations and Localization of Fastening Locations

In one example, to enable fastening of respective front and rear fastener components 56, 57 of the insert 50 with respective front and rear attachment zones 33, 32 on the outer cover 20, respective fastening pairs 56, 33 and 57, 32 may include cooperating fastener components. An example of a suitable hook-and-loop fastening system is a VELCRO system, a product of Velcro Industries B.V., components of which are available from Velcro USA, Inc., Manchester, N.H.

However, fastening pairs 56, 33 and 57, 32 need not necessarily include respective components of a hook-and-loop fastening system, and need not necessarily include respective components of a two-component fastening system. Rather, a fastening system may require only one fastener component, or use other types of fastener components. The fastener components used may be adapted to engage, retain, and otherwise hold the insert 50 or a portion thereof. An attachment zone on the outer cover 20 may include a patch of adhesive; a structure having a region of relatively high coefficient of friction; a pocket; flap; strap; or other capturing, holding and/or retaining surface, device or structure. Thus, referring to FIG. 2C in one example, the inside of the outer cover 20 may include one or more pocket structures 32a, 33a situated on or along the inner surface 25 of the outer cover 20, in, e.g., the front waist region 27 or rear waist region 28. Such a pocket structure may have an opening facing downward or upward (relative to the wearer in a standing position, and relative to FIG. 2B). A pocket structure may be adapted to receive, fit and capture, for example, the forward edge and a portion of the forward region 54 of the insert 50. A pocket structure 32a, 33a may have an opening facing the lateral axis 45, such that an end of the insert 50 may be inserted therein and retained thereby. A pocket structure may alternatively have an opening facing away from the lateral axis 45, such that an end of the insert 50 may be inserted therein and retained thereby, and then the insert 50 may be folded back over such opening and toward the lateral axis 45.

Insert End Support Stiffeners

In an embodiment, referring to FIGS. 3 and 4, an end support stiffener 60 and/or 62 may be included at one or both ends of the insert 50. Such an end support stiffener may serve to aid the user in engaging the insert 50 with the outer cover 20, and to help the insert 50 maintain its intended shape and configuration while being worn beneath an outer cover, i.e., help maintain its intended shape, position and gasketing functions (e.g., of the standing cuffs 53). An end support stiffener 60, 62 also may help control the corners of the insert 50 regardless of the size, type or location of fastener components included on the insert 50. In addition to providing resistance to longitudinal pull of the cuff edges 58, the end support stiffeners 60, 62 may provide resistance to bending in any direction or plane. An end support stiffener 60, 62 may be affixed to, or incorporated within, the insert 50 proximate one or both ends thereof as suggested by FIGS. 3 and 4.

Referring to FIG. 4, one or more of the end support stiffeners 60, 62 may be disposed in a lateral orientation with respect to the insert 50 and formed of any flat, sheet-like or card-like material, or any flat, stiffened assembly that adds stiffness to the insert end that exceeds the stiffness of the adjacent portion lying nearer the insert lateral axis 70.

Fastening Zone Configurations on the Outer Cover

Referring again to FIG. 1B, as an example, the first and second fastening zones positioned on opposing side of the longitudinal axis 46 may have various configurations that allow for easier fastening, more secure fastening, and/or better fastening. Each side of the fastening zones (e.g., 31 and 30 or 31' and 30') may each have two or more portions configured to be joined with another side of the fastening zones divided into two or more portions. Stated another way, the first side of the fastening zone 31 or 31' may have two or more portions and those two or more portions may be joined with the second side of the fastening zone 30 or 30' having two or more portions. The two or more portions on each side of the fastening zones may be joined to each other to join the fastening zone. Various configurations of the two or more portions are described in further detail below.

Fastening Component Configurations

Figure 6:
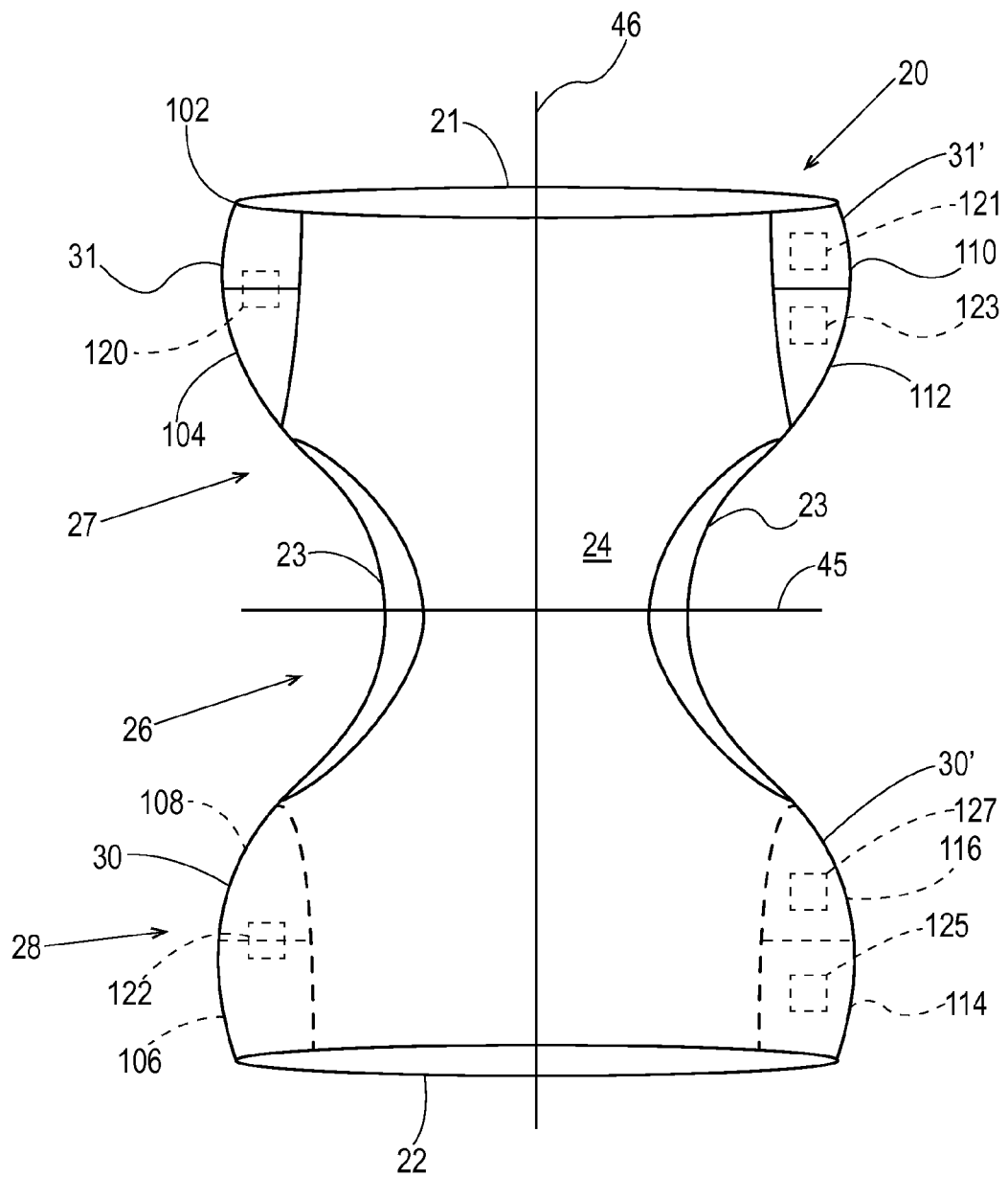
FIGS. 6-12 are plan views of outer covers opened and laid flat, outer surfaces facing (i.e., garment-facing surfaces) the viewer in accordance with various non-limiting embodiments of the present disclosure.

In an embodiment, referring to FIG. 6, an outer cover 20 is illustrated with the garment-facing surface 24 oriented toward the viewer. The outer cover 20 may comprise a first fastening zone comprising a first side 31 in the front waist region 27 and a second side 30 in the rear waist region 28 and a second fastening zone comprising a first side 31' in the front waist region 27 and a second side 30' in the rear waist region 28. The first fastening zone is positioned on an opposite side of the longitudinal axis 46 as the second fastening zone. The first sides 31 and 31' may be positioned on opposite sides of the longitudinal axis 46 and, likewise, the second sides 30 and 30' may be positioned on opposite sides of the longitudinal axis 46. The first side 31 of the first fastening zone may comprise a first portion 102 and a second portion 104. Likewise, the second side 30 of the first fastening zone may comprise a first portion 106 and a second portion 108. In the claims, the first portion 106 and the second portion 108 may be referred to as the third and fourth portions, respectively, of the second side 30 of the first fastening zone for clarity. The first side 31' of the second fastening zone may comprise a first portion 110 and a second portion 112. The second side 30' of the second fastening zone may comprise a first portion 114 and a second portion 116. In the claims, the first portion 114 and the second portion 116 may be referred to as the third and fourth portions, respectively, of the second side 30' of the second fastening zone for clarity. In the example embodiment of FIG. 6, the first portions may be positioned longitudinally outboard of the second portions and may be positioned adjacent to the second portions. The first portions 102 and 110 may be positioned proximate to or adjacent to the front waist edge 21 and the first portions 106 and 114 may be positioned proximate to or adjacent to the rear waist edge 22. The second portions 104, 112, 108, and 116 may be positioned proximate to or adjacent to one of the leg opening edges 23.

In any embodiments of the present disclosure, the first and second portions may also be positioned at any other suitable locations within the first and second fastening zones. Each of the first and second portions may have any suitable size and shape. In an embodiment, each of the first portions may have the same size and shape or may have a different size and shape. Each of the second portions may have the same features. In various embodiments, each of the first portions may have the same size and shape as the second portions or may have a different size and shape.

Figure 7:
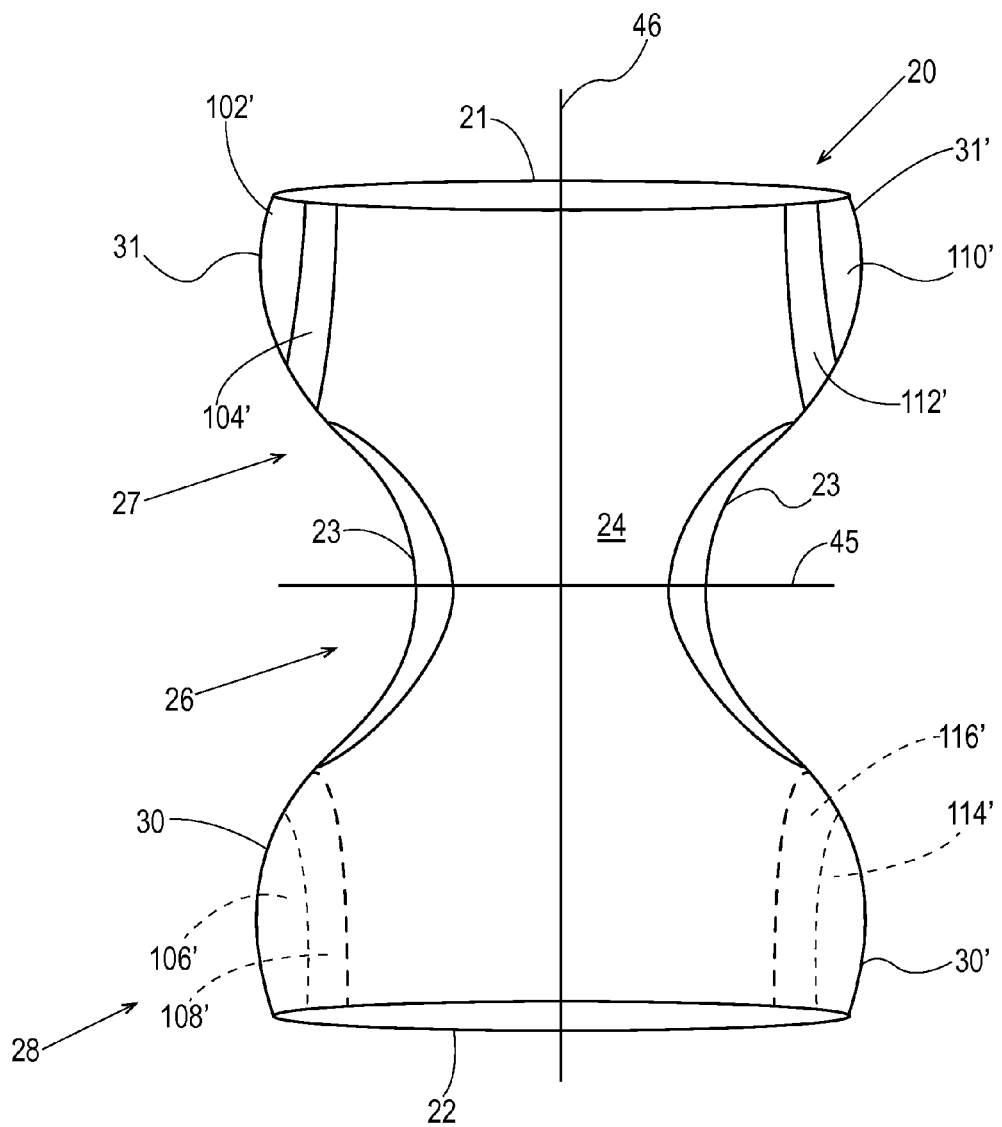

Referring to FIG. 7, the first side 31 of the first fastening zone may comprise a first portion 102' and a second portion 104'. Likewise, the second side 30 of the first fastening zone may comprise a first portion 106' and a second portion 108'. In the claims, the first portion 106' and the second portion 108' may be referred to as the third and fourth portions, respectively, of the second side 30 of the first fastening zone for clarity. The first side 31' of the second fastening zone may comprise a first portion 110' and a second portion 112'. The second side 30' of the second fastening zone may comprise a first portion 114' and a second portion 116'. In the claims, the first portion 114' and the second portion 116' may be referred to as the third and fourth portions, respectively, of the second side 30' of the second fastening zone for clarity. In the example embodiment of FIG. 7, the first portions may be positioned laterally outboard of the second portions and may be positioned adjacent to the second portions.

Figure 8:
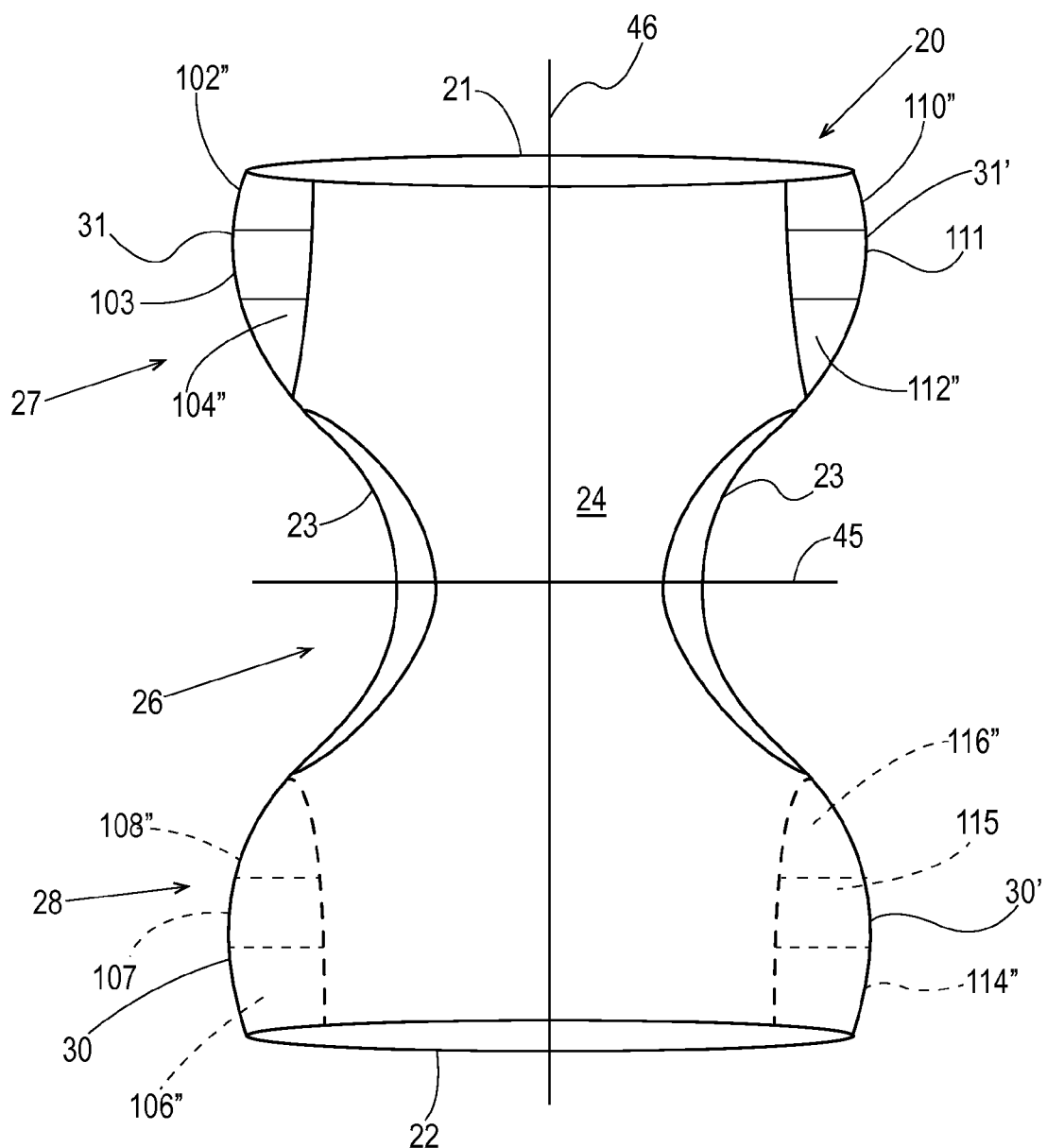

Referring to FIG. 8, the first side 31 of the first fastening zone may comprise a first portion 102", a second portion 104", and a third portion 103. Likewise, the second side 30 of the first fastening zone may comprise a first portion 106", a second portion 108", and a third portion 107. The third portion 103 may be positioned intermediate, longitudinally intermediate, laterally intermediate, or at least partially intermediate, the first portion 102" and the second portion 104". The third portion 107 may be positioned intermediate, longitudinally intermediate, laterally intermediate, or at least partially intermediate the first portion 106" and the second portion 108". In the claims, the first portion 106", the second portion 108", and the third portion 107 may be referred to as the fourth, fifth, and sixth portions, respectively, of the second side 30 of the first fastening zone for clarity. The first side 31' of the second fastening zone may comprise a first portion 110", a second portion 112", and a third portion 111. The second side 30' of the second fastening zone may comprise a first portion 114", a second portion 116", and a third portion 115. The third portion 111 may be positioned intermediate, longitudinally intermediate, laterally intermediate, or at least partially intermediate, the first portion 110" and the second portion 112". The third portion 115 may be positioned intermediate, longitudinally intermediate, laterally intermediate, or at least partially intermediate the first portion 114" and the second portion 116". In the claims, the first portion 114", the second portion 116", and third portion 115 may be referred to as the fourth, fifth, and sixth portions of the second side 30' of the second fastening zone for clarity.

FIGS. 6-8 are merely some example configurations of the various portions of the first and second fastening zones. It is to be understood that the various portions may have any suitable configuration, size, dimension, and/or shape. Furthermore, more than 3 portions may be provided on sides of a fastening zone. In an embodiment, one side of a fastening zone may have a different numbers of portions as the other side of the fastening zone. In such an embodiment, less than all of the portions may be used to accomplish fastening, for example, depending on caregiver preferences.

Referring again to FIG. 6, the first portion 102 may comprise a first fastening component and the second portion 104 may comprise a second fastening component forming a first side of the fastening zone. The first portion 106 may comprise a first fastening component and the second portion 108 may comprise a second fastening component forming a second side of the fastening zone. The first and second fastening components on the first portion 106 and the second portion 108 may be referred to as the third and fourth fastening components, respectively, in the claims for clarity. Although FIG. 6 is being referred to in this example embodiment, the example embodiments of the present disclosure may also apply. The first and third fastening components may have a first fastening property. The second and fourth fastening components may have a second fastening property. The first and second fastening properties may be the same, similar, or different. The first and third fastening components may be configured to be joined to each other and the second and fourth fastening components may configured to be joined to each other to form a closed fastening zone. The second fastening zone may have the same features, similar features, or different features as the first fastening zone described in this paragraph.

The fastening properties referred to above may be geometries of the fastening components, areas of the fastening components, dimensions of the fastening components, fastening forces between the first fastening component and the third fastening component and/or the second fastening component and the fourth fastening component, the fastening mechanisms (e.g., snaps, magnets, hook and loop materials) on the fastening components, and/or the fastening types (e.g., discrete fastener, securing fastener, adjustable fastener) of the fastening components. The fastening properties of the fastening components may also comprise patterns, textures, and/or colors. The patterns, textures, and/or colors thereof may be the same, similar, and/or different. For example, a first fastening component may have the same color as a second fastening component, but may have a different pattern and/or texture.

In an example embodiment, referring again to FIG. 6, the first fastening component on the first portion 102 may comprise one or more hook materials or loop materials and the first (or third) fastening component on the first (or third) portion 106 may comprise one or more of the other of loop materials or hook materials. The second fastening component on the second portion 104 may comprise one or more magnets, magnetic components, or sides of snaps and the second (or fourth) fastening component on the second (or fourth) portion 108 may comprise one or more magnetically attractable materials, magnets, magnetic components, or the other sides of the snaps. In another embodiment, the first fastening component on the first portion 102 may comprise one or more magnets, magnetic components, or sides of snaps and the first (or third) fastening component on the first (or third) portion 106 may comprise one or more magnetically attractable materials, magnets, magnetic components, or the other sides of the snaps. The second fastening component on the second portion 104 may comprise one or more hook materials or loop materials and the second (or fourth) fastening component on the second (or fourth) portion 108 may comprise one or more of the other of loop materials or hook materials.

In another example embodiment, referring again to FIG. 6, the first fastening component on the first portion 102 may have a blue color and the first (or third) fastening component on the first (or third) portion 106 may have a blue color. The second fastening component on the second portion 104 may have a red color and the second (or fourth) fastening component on the second (or fourth) portion 108 may have a red color. In another example embodiment, the first fastening component on the first portion 102 may have a first pattern and/or texture and the first (or third) fastening component on the first (or third) portion 106 may have the first pattern and/or texture. The second fastening component on the second portion 104 may have a second different pattern and/or texture and the second (or fourth) fastening component on the second (or fourth) portion 108 may have the second different pattern and/or texture. Such features may instruct caregivers on the appropriate joining of the various fastener components.

Again referring to FIG. 6, the side of the first fastening zone in the front waist region 27 may comprise a first side of a self-aligning fastener 120 and the side of the first fastening zone in the rear waist region 28 may comprise a second side of the self-aligning fastener 122. The first side of the self-aligning fastener 120 may be positioned in the first portion 102, the second portion 104, or may extend into the first portion 102 and the second portion 104. Likewise, the second side of the self-aligning fastener 122 may be positioned in the first portion 106, the second portion 108, or may extend into the first portion 106 and the second portion 108. The second fastening zone may have the same, similar, or different self-aligning fasteners as the first fastening zone. In other embodiments, the second fastening zone may not comprise a self-aligning fastener.

It will be understood herein that, in at least some embodiments, the first fastening zone may have the features described herein and that the second fastening zone may be a permanent side seam or a prefastened (i.e., at the manufacturer) side seam. Of course, the opposite is also within the scope of the present disclosure. In other embodiments, only a portion of one or both of the side seams may be permanent with the other portion(s) being joined using the features described herein.

Self-aligning fastener, as used herein, means a fastener having a first side and a second side which mate to form the fastener. The first side is attracted to the second side, the second side is attracted to the first side, or the first and second sides are attracted to each other by, for example, magnetic attraction. In an example embodiment having two magnets on opposite sides of the fastener, each magnet would attract the other (positive to negative pole). In an example embodiment having a magnet and a ferrous metal on opposite sides of the fastener, the magnet would attract the metal, but not vice versa. In any event, at least one side of the fastener attracts the other side. When the first side is positioned proximate to the second side, the two sides of the fastener begin to join over a distance (e.g., a distance of 2 inches or 1 inch or less) to self-align the sides of the fastening zone or outer cover/insert fastener components on which the self-aligning fasteners are positioned. Physical contact between the first side and the second side is not required for the first and second sides to attract each other, only proximity such that the first side and the second side may "seek" each other.

In an embodiment, using the second fastening zone of FIG. 6 as an example, the side of the second fastening zone in the front waist region 27 may comprise a first side of a first self-aligning fastener 121 and a first side of a second self-aligning fastener 123 and the side of the second fastening zone in the rear waist region 28 may comprise a second side of a first self-aligning fastener 125 and a second side of a self-aligning fastener 127. The first side of the first self-aligning fastener 121 may be positioned in the first portion 110 and the first side of the second self-aligning fastener 123 may be positioned in the second portion 112. Likewise, the second side of the first self-aligning fastener 125 may be positioned in the first portion 114 and the second side of the second self-aligning fastener 127 may be positioned in the second portion 116. The self-aligning fasteners 121 and 125 may be joined to each other and the self-aligning fasteners 123 and 127 may be joined to each other to close, or at least partially, close the waist opening. The first fastening zone may have the same, similar, or different self-aligning fasteners as the second fastening zone or may not have any self-aligning fasteners. In various embodiments, the self-aligning fasteners may be positioned at any suitable locations on the various portions.

The various self-aligning fasteners may be positioned under the fastening components (e.g., under the first fastening component on the first portion 102). Stated another way, the self-aligning fasteners may be internal to the portions (i.e., not on the wearer-facing surface or on the garment-facing surface) of the sides of the fastening zones. In another embodiment, the self-aligning fasteners may be positioned on the garment-facing surface or on the wearer-facing surface. The self-aligning fasteners may have any suitable size and shape and may be made of any suitable materials. A side of a self-aligning fastener on a first side of the first fastening zone may have the same size and/or shape, or a different size and/or shape as the other side of the self-aligning fastener on a second side of the first fastening zone.

The self-aligning fasteners may be used to initially align, or at least partially align, non-self aligning fasteners of the sides of the fastening zones, especially when the outer cover 20 is in a pant form. Typically, the pant is donned when the wearer is in the standing position. As such, a caregiver can easily align the non-self aligning fasteners using the self-aligning fasteners when forming the outer cover 20 into a pant prior to donning or when applying the outer cover 20 to a wearer in the standing position. The non-self aligning fasteners may then be used to further secure the outer cover to the wearer and/or to adjust the outer cover on the wearer.

In various embodiments, the self-aligning fasteners may be independent of or formed of a different material than the fastening components on the various portions. The self-aligning fasteners may comprise magnets, magnetic components, and/or magnets and magnetically attractable materials, such as metals, ferrous materials, or other magnetizable metals or materials. Any suitable magnets, magnetic components, and magnetically attractable materials known to those of skill in the art are within the scope of the present disclosure. In an embodiment, a first side of a self-aligning fastener may be a magnetic component and a second side of the self-aligning fastener may be a magnetic component or may be a magnetically attractable material.

Figure 9:
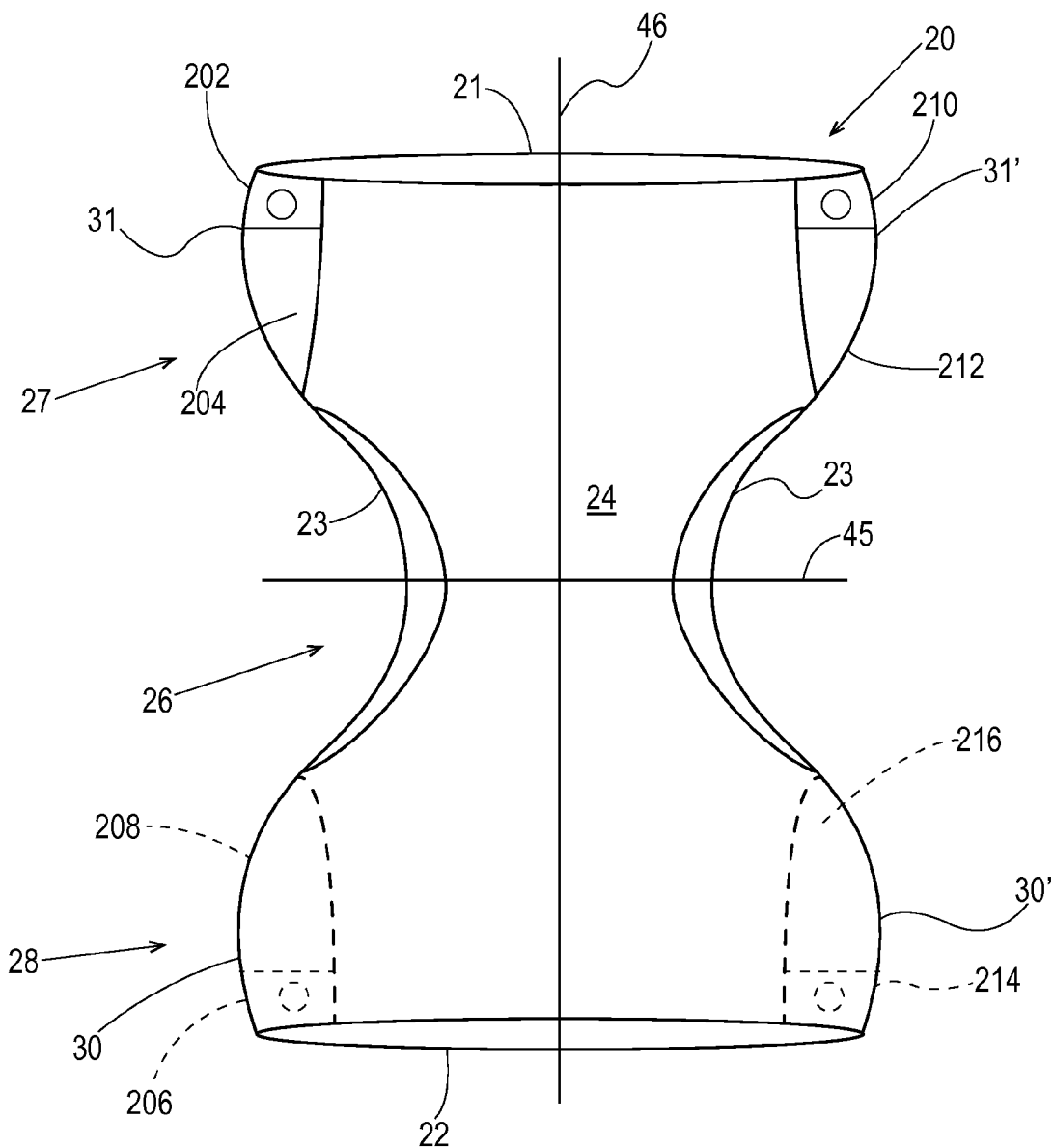

In an embodiment, referring to FIG. 9, a first side of the first fastening zone on the front waist region 27 may comprise a first portion 202 and a second portion 204 and the second side of the first fastening zone on the rear waist region 28 may comprise a first portion 206 (or third portion) and a second portion 208 (or fourth portion). The first portion 202 may comprise a first fastening component forming a side of a discrete fastener and the first portion 206 may comprise a first fastening component (or third fastening component) forming the other side of the discrete fastener. The second portion 204 may comprise a second fastening component forming a side of an adjustable fastener and the second portion 208 may comprise a second fastening component (or fourth fastening component) forming the other side of the adjustable fastener. The first fastening component on the first portion 202 may be joined with the first fastening component on the first portion 206 to form the discrete fastener and the second fastening component on the second portion 204 may be joined with the second fastening component on the second portion 208 to form the adjustable fastener. A side of a discrete fastener may be positioned adjacent to, proximate to, and/or be surrounded by a side of an adjustable fastener in a side of a fastening zone. In one embodiment, the discrete fasteners may be positioned proximate to the waist edges 21 and 22 and the adjustable fasteners may be positioned proximate to the leg opening edges 23 or vice versa. The discrete fasteners may be positioned longitudinally outboard, longitudinally inboard, laterally outboard, or laterally inboard of the adjustable fasteners. Any suitable number of discrete fasteners and/or adjustable fasteners may be provided in a fastening zone. The first and second portions discussed in this embodiment may have any of the features discussed above with respect to FIGS. 6-8. Furthermore, the second fastening zone of FIG. 9 may have the same, similar, or different features as discussed in this paragraph with respect to the first fastening zone. In other embodiments, the second fastening zone may have different features.

Discrete fasteners, as used herein, means fasteners having a first side and a second side that attach to each other at predetermined locations within the fastening zones and/or on the outer cover/insert fastener components (i.e., no or limited caregiver options). Some non-limiting examples of discrete fasteners are snaps, buttons in combination with button-receiving slots, hooks in combination with hook engaging features, magnets, magnetic components, and magnetically attractable materials in combination with magnets or magnetic components. The sides of discrete fasteners typically attach to each other at discrete locations. One or more sides of the discrete fasteners may be discrete arrays (e.g., a first side of a snap on one side and three other sides of the snap on the other side). Discrete fasteners, such as snaps, for example, may permit rotational movement/adjustability of a portion of a fastening zone by pivoting (i.e., one side of the snap may be permitted to rotate relative to the other side of the snap). A securing or adjustable fastener in the same fastening zone or region as the discrete fastener may be grasped, rotated or moved so as to pivot the snap, and then joined to the other side of the securing or adjustable fastener.

Adjustable fasteners, as used herein, means fasteners that may have their two respective sides attached to each other at a plurality of locations (i.e., caregiver options). Examples of adjustable fasteners are hook materials in combination with loop materials, hooks in combination with a plurality of hook engaging features, buttons in combination with a plurality of button-receiving slots, adhesives, and/or cohesives. Adjustable fasteners provide the caregiver with the ability to attach the sides of a fastening zone at a plurality of locations to provide preferred fit and/or comfort when engaged with a lower torso of the wearer. In other instances, the adjustable fasteners may provide the caregiver with the ability to attach the insert's fastener components to the outer cover's insert fastener components in desirable locations to provide improved comfort and fit to a wearer when the insert is attached to the outer cover. In some instances, adjustable fasteners may be attached subsequent to the fastening of discrete fasteners and/or self-aligning fasteners.

In use, the caregiver would likely attach the discrete fasteners or self-aligning fasteners (e.g., snaps, magnetic components) together first and then use the adjustable fasteners to achieve the proper fit and comfort of the outer cover 20 on the wearer. By providing discrete fasteners or self-aligning fasteners, a caregiver can easily attach the first and/or second fastening zones of the outer cover 20 prior to donning the outer cover 20 on the wearer or when donning the outer cover 20 on the wearer when the wearer is in the standing position. The caregiver can then use the adjustable fasteners to achieve proper fit and/or comfort of the outer cover 20 on the wearer.

Figure 10:
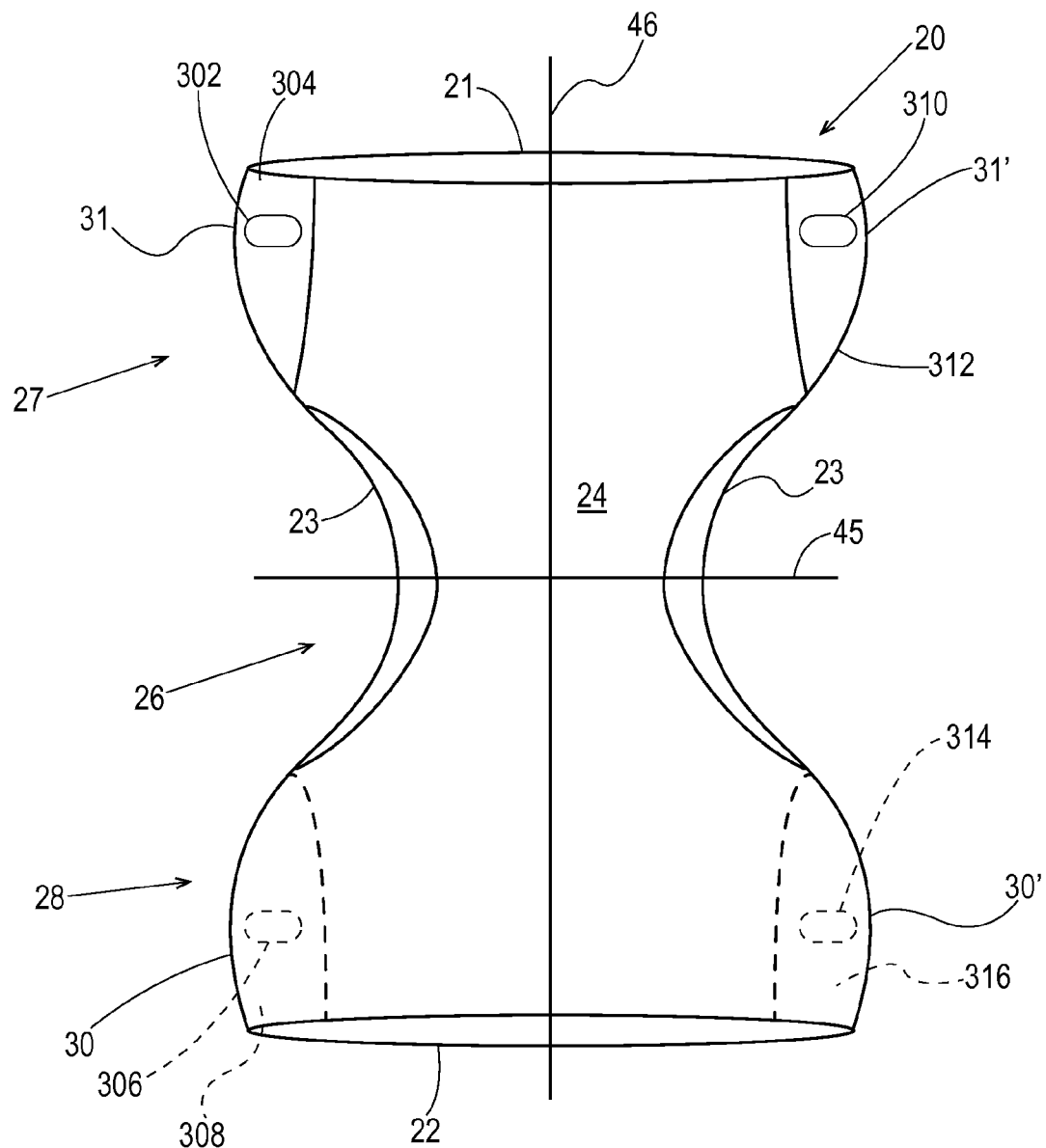

In an embodiment, referring to FIG. 10, a first side of the first fastening zone on the front waist region 27 may comprise a first portion 302 and a second portion 304 and a second side of the first fastening zone on the rear waist region 28 may comprise a first portion 306 (or third portion) and a second portion 308 (or fourth portion). The first portion 302 may comprise a first fastening component forming a side of a self-aligning fastener (e.g., a magnet) and the first portion 306 may comprise a first fastening component (or third fastening component) forming the other side of the self-aligning fastener (e.g., a magnet or magnetically attractable material). The second portion 304 may comprise a first fastening component forming a side of a securing fastener (e.g., hook or loop material) and the second portion 308 may comprise a second fastening component (or fourth fastening component) forming the other side of the securing fastener (e.g., the other of the hook or loop material). The first fastening component on the first portion 302 may be joined with the first fastening component on the first portion 306 to form the self-aligning fastener and the second fastening component on the second portion 304 may be joined with the second fastening component on the second portion 308 to form the securing fastener. A side of a self-aligning fastener may be positioned adjacent to, proximate to, and/or be surrounded by a side of a securing fastener in a side of a fastening zone. In one embodiment, the self-aligning fasteners may be positioned at any suitable locations within the first fastening zone. In an embodiment, a plurality of self-aligning fasteners may be provided in the first and second fastening zones along with one or more securing fasteners. The self-aligning fasteners may have any suitable size and/or shape. The second fastening zone of FIG. 10 may have the same, similar, or different features as discussed in this paragraph with respect to the first fastening zone. In other embodiments, the second fastening zone may have different features.

Securing fastener, as used herein, means a fastener that is used to retain the waist region of an outer cover in the closed position. The securing fastener may be hook and loop materials, buttons and button-receiving slots, or hooks and hook receiving components, for example. Typically, the securing fastener may be used after attachment of a discrete fasteners or a self-aligning fastener. The self-aligning fasteners or the discrete fasteners may hold two sides of a fastening zone together and align those two sides until a securing fastener can be used to firmly close the waist region.

Figure 11:
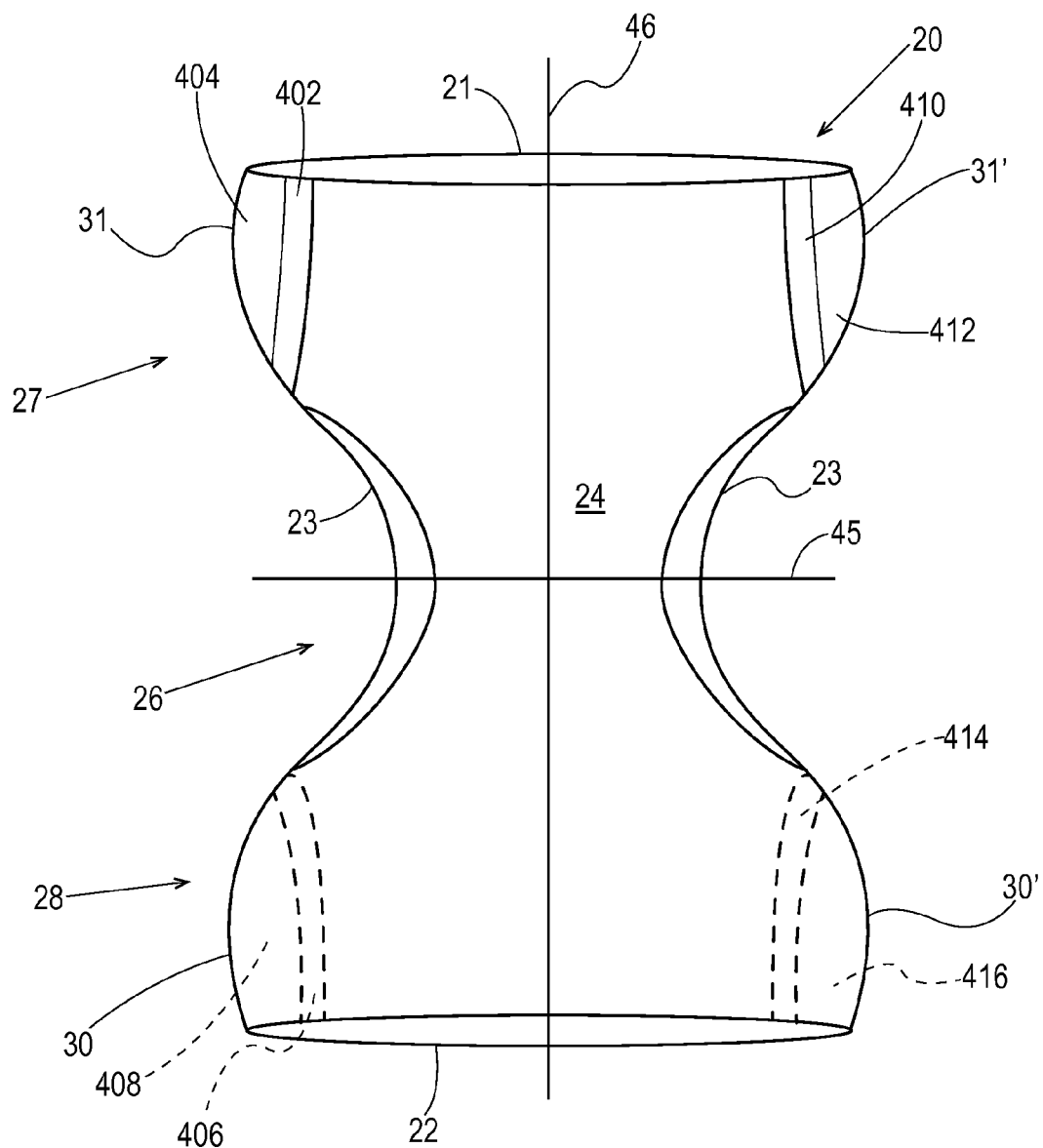

In an embodiment, referring to FIG. 11, a first side of the first fastening zone on the front waist region 27 may comprise a first portion 402 and a second portion 404 and a second side of the first fastening zone on the rear waist region 28 may comprise a first portion 406 (or third portion) and a second portion 408 (or fourth portion). The first portion 402 may comprise a first fastening component forming a side of a self-aligning fastener or a discrete fastener and the first portion 406 may comprise a first fastening component (or third fastening component) forming the other side of the self-aligning fastener or the discrete fastener. The second portion 404 may comprise a first fastening component forming a side of a securing fastener or an adjustable fastener and the second portion 408 may comprise a second fastening component (or fourth fastening component) forming the other side of the securing fastener or the adjustable fastener. The first and second portions may also be reversed (i.e., first portions 402 and 406 with a securing fastener or an adjustable fastener and second portions 404 and 408 with a self-aligning fastener or a discrete fastener). The first fastening component on the first portion 402 may be joined with the first fastening component on the first portion 406 to form the self-aligning fastener or the discrete fastener and the second fastening component on the second portion 404 may be joined with the second fastening component on the second portion 408 to form the securing fastener or the discrete fastener. A side of a self-aligning fastener or a discrete fastener may be positioned adjacent to, proximate to, and/or be surrounded by a side of a securing fastener or an adjustable fastener in a side of a fastening zone. In one embodiment, the self-aligning fasteners or discrete fasteners may be positioned at any suitable locations within the first fastening zone. In an embodiment, a plurality of self-aligning fasteners or discrete fasteners may be provided in the first and second fastening zones along with one or more securing fasteners or adjustable fasteners. The self-aligning fasteners or discrete fasteners may have any suitable size and/or shape. The second fastening zone of FIG. 11 may have the same, similar, or different features as discussed in this paragraph with respect to the first fastening zone. In other embodiments, the second fastening zone may have different features.

Figure 12:
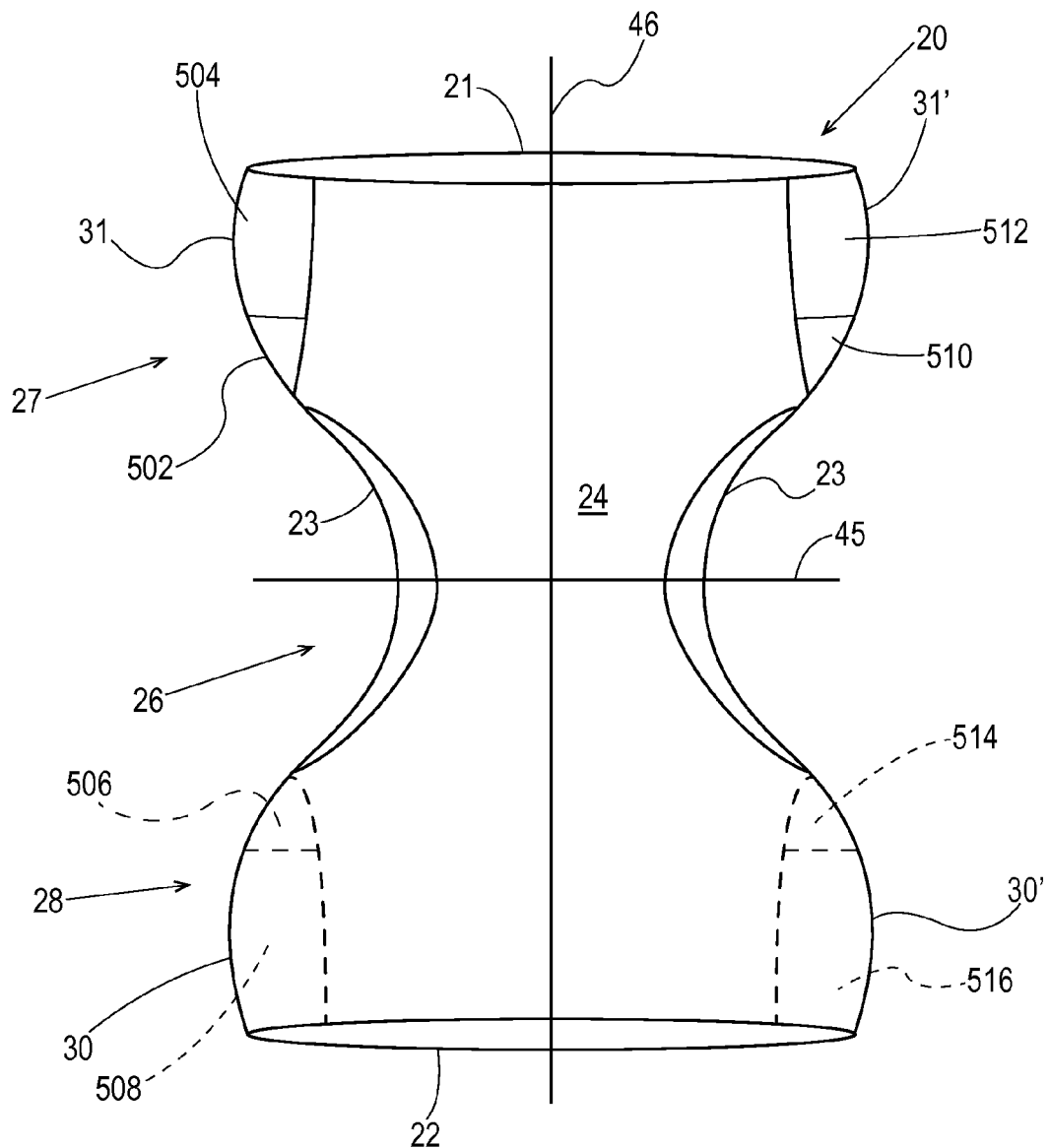

In an embodiment, referring to FIG. 12, a first side of the first fastening zone on the front waist region 27 may comprise a first portion 502 and a second portion 504 and a second side of the first fastening zone on the rear waist region 28 may comprise a first portion 506 (or third portion) and a second portion 508 (or fourth portion). The first portion 502 may comprise a first fastening component forming a side of a self-aligning fastener or a discrete fastener and the first portion 506 may comprise a first fastening component (or third fastening component) forming the other side of the self-aligning fastener or the discrete fastener. The second portion 504 may comprise a first fastening component forming a side of a securing fastener or an adjustable fastener and the second portion 508 may comprise a second fastening component (or fourth fastening component) forming the other side of the securing fastener or the adjustable fastener. The first fastening component on the first portion 502 may be joined with the first fastening component on the first portion 506 to form the self-aligning fastener or the discrete fastener and the second fastening component on the second portion 504 may be joined with the second fastening component on the second portion 508 to form the securing fastener or the discrete fastener. A side of a self-aligning fastener or a discrete fastener may be positioned adjacent to, proximate to, and/or be surrounded by a side of a securing fastener or an adjustable fastener in a side of a fastening zone. In one embodiment, the self-aligning fasteners or discrete fasteners may be positioned at any suitable locations within the first fastening zone. In an embodiment, a plurality of self-aligning fasteners or discrete fasteners may be provided in the first and second fastening zones along with one or more securing fasteners or adjustable fasteners. The self-aligning fasteners or discrete fasteners may have any suitable size and/or shape. The second fastening zone of FIG. 12 may have the same, similar, or different features as discussed in this paragraph with respect to the first fastening zone. In other embodiments, the second fastening zone may have different features.

Figure 13:
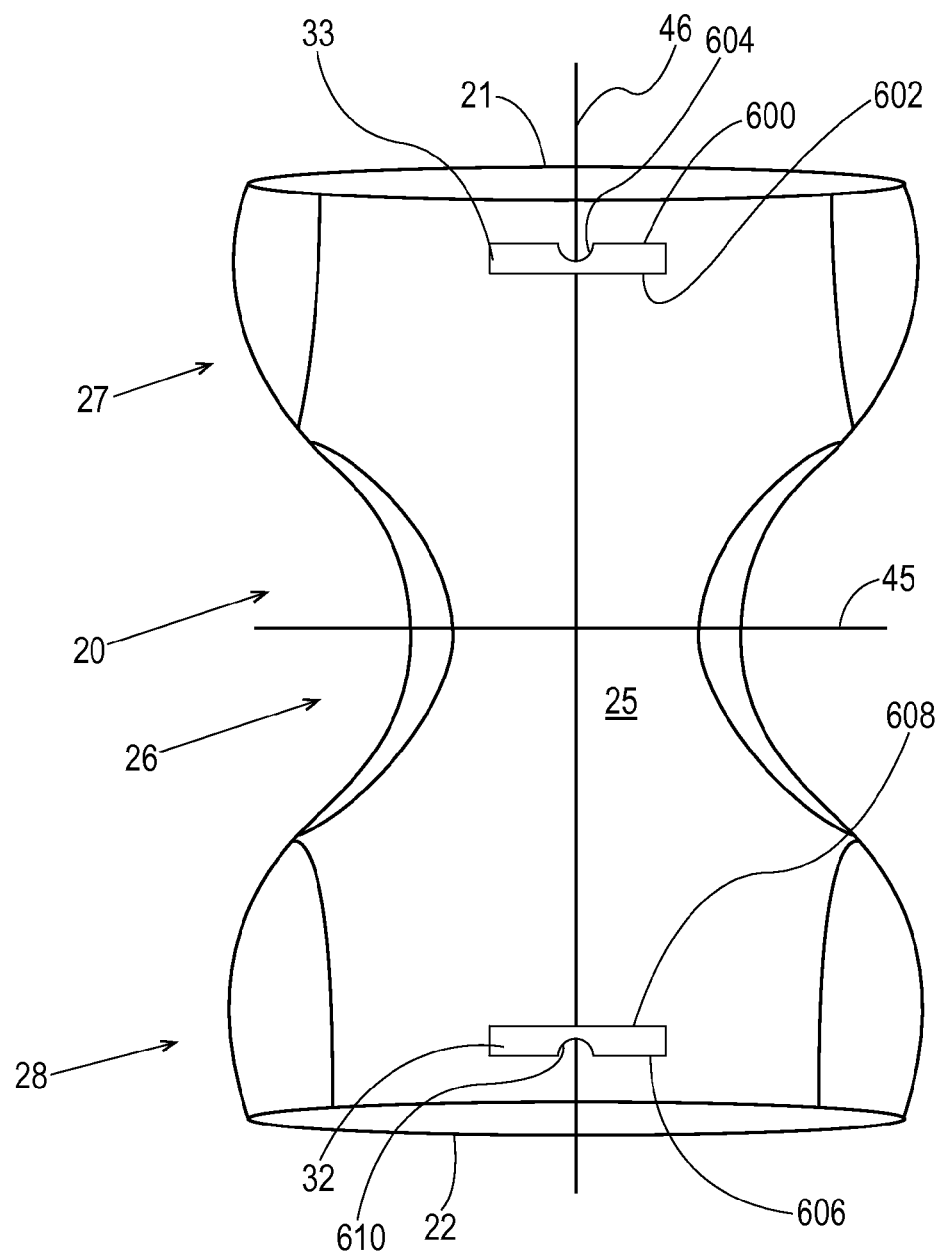
FIGS. 13-16 are plan views of reusable outer covers opened and laid flat, inner, wearer-facing surface oriented towards the viewer in accordance with various non-limiting embodiments of the present disclosure.

In an embodiment, referring to FIG. 1C, an example wearable absorbent article 10 is illustrated. The wearable absorbent article 10 may comprise a reusable outer cover 20 and a disposable absorbent insert 50. The disposable absorbent insert 50 may be attached to and removed from the reusable outer cover 20. Referring to FIG. 13, an example reusable outer cover 20 is illustrated with its inner, wearer-facing surface 25 oriented towards the viewer. The reusable outer cover 20 may comprise a front waist region 27, a rear waist region 28, and a crotch region 26 disposed intermediate the front waist region 27 and the rear waist region 28. The reusable outer cover 20 may comprise a waist opening edge represented by reference numbers 21 and 22 together (see e.g., FIG. 1C). The waist opening edge 21 and 22 may define a waist opening circumference of the reusable outer cover 20 when the reusable outer cover 20 is in a closed configuration (see e.g., FIG. 1C). The reusable outer cover 20 may comprise a first insert fastener component 33 in the front waist region 27 proximate to the waist opening edge 21. The first insert fastener component 33 may comprise a first end or edge 600 positioned most proximate to the waist opening edge 21 and a second end or edge 602 positioned most distal from the waist opening edge 21. The first end 600 is positioned more longitudinally outboard than the second end 602 relative to the lateral axis 45. An insert-gripping recess 604 may be formed in the first end 600 and/or another portion of the insert fastener component 33 in an area covering the longitudinal axis 46 of the reusable outer cover 20 or in another area not covering the longitudinal axis 46 (i.e., offset on one side or the other from the longitudinal axis 46). The reusable outer cover 20 may also comprise a second insert fastener component 32 in the rear waist region 28 proximate to the waist opening edge 22. The second insert fastener component 32 may comprise a first end or edge 606 positioned most proximate to the waist opening edge 22 and a second end or edge 608 positioned most distal from the waist opening edge 22. The first end 606 is positioned more longitudinally outboard than the second end 608 relative to the lateral axis 45. An insert-gripping recess 610 may be formed in the first end 606 or another portion of the insert fastener component 32 in an area covering the longitudinal axis 46 of the reusable outer cover 20 or in another area not covering the longitudinal axis 46 (i.e., offset on one side or the other from the longitudinal axis 46). The insert-gripping recesses 604 and 610 may have the same size, shape, dimensions, and/or area or may have different sizes, shapes, dimensions, and/or areas. In an embodiment, only one insert fastener component may have an insert-gripping recess. In still other embodiments, one or more insert fastener components may each define more than one insert-gripping recess therein or in a perimeter, end, or edge thereof In an embodiment, the first end 600 may be positioned between 0.1 inches and 5 inches from the waist opening edge 21 and, likewise, the first end 606 may be positioned between 0.1 inches and 5 inches from the waist opening edge 22, specifically reciting all 0.1 inch increments within the specified ranges and all ranges formed therein or thereby. The spacing of each first end 600 and 606 relative to its respective portion of the waist opening edge 21 or 22 may be the same, similar, or different. The ranges specified in this paragraph specify what the term "proximate" means in the claims, when used in reference to the first ends 600 and 606 relative to their respective waist opening edges 21 and 22.

Figure 14:
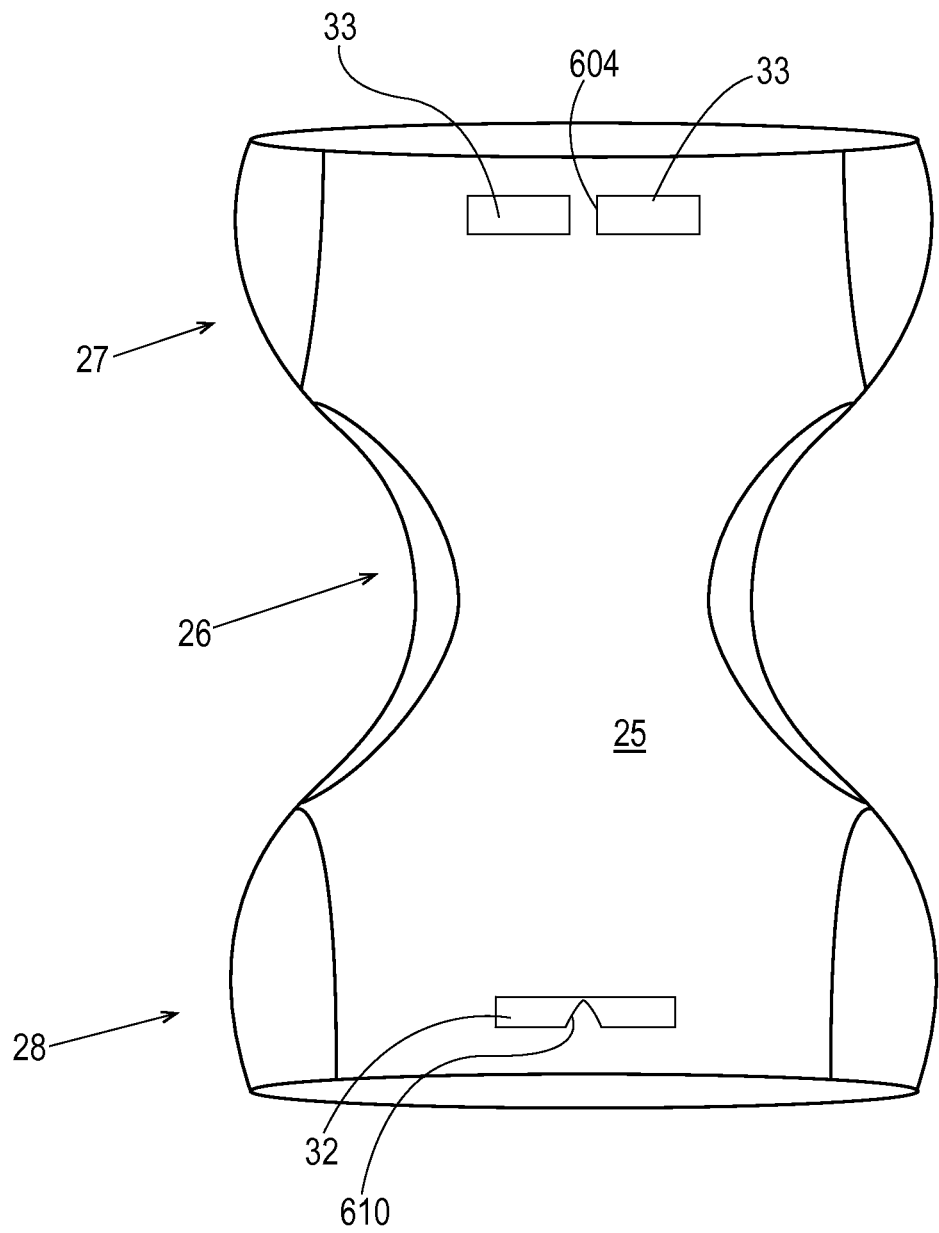
Figure 15:
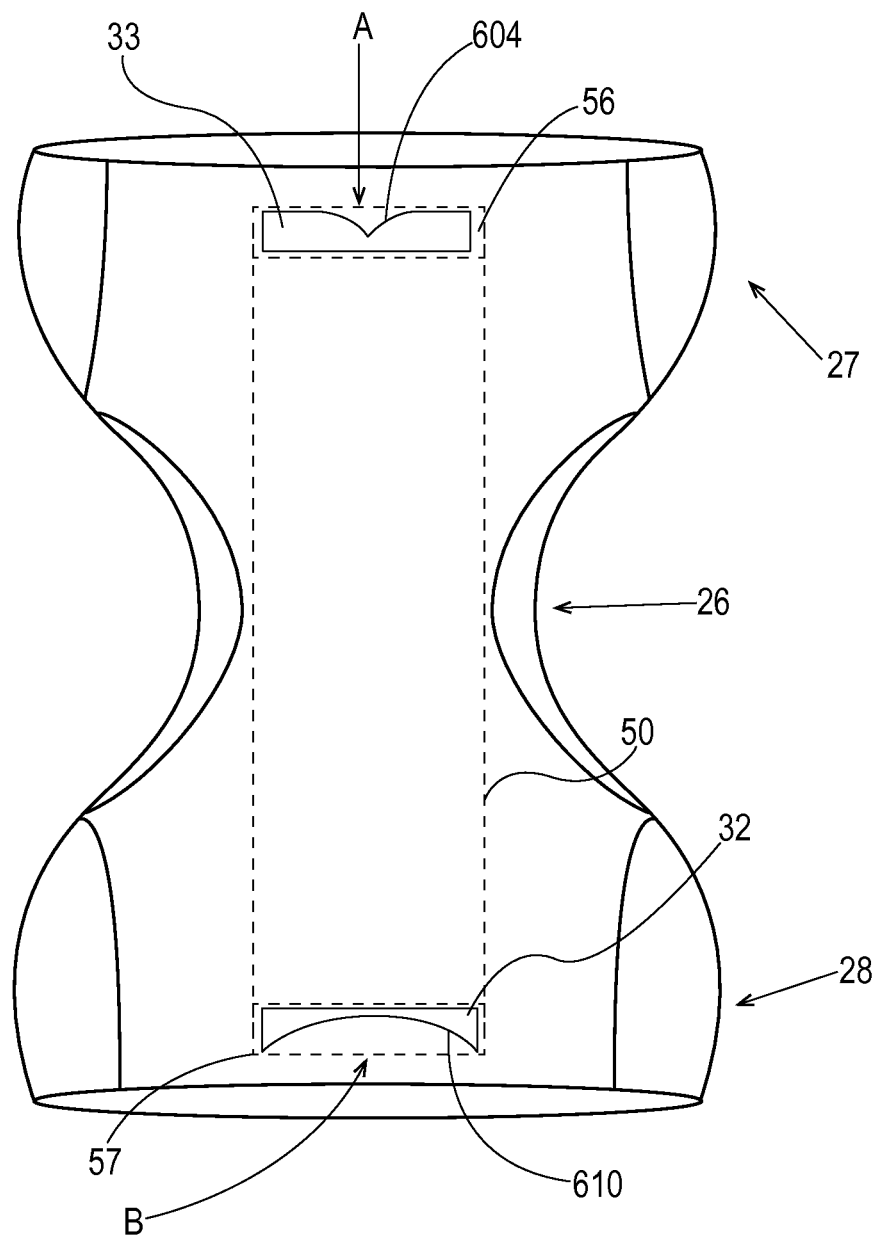
Figure 16:
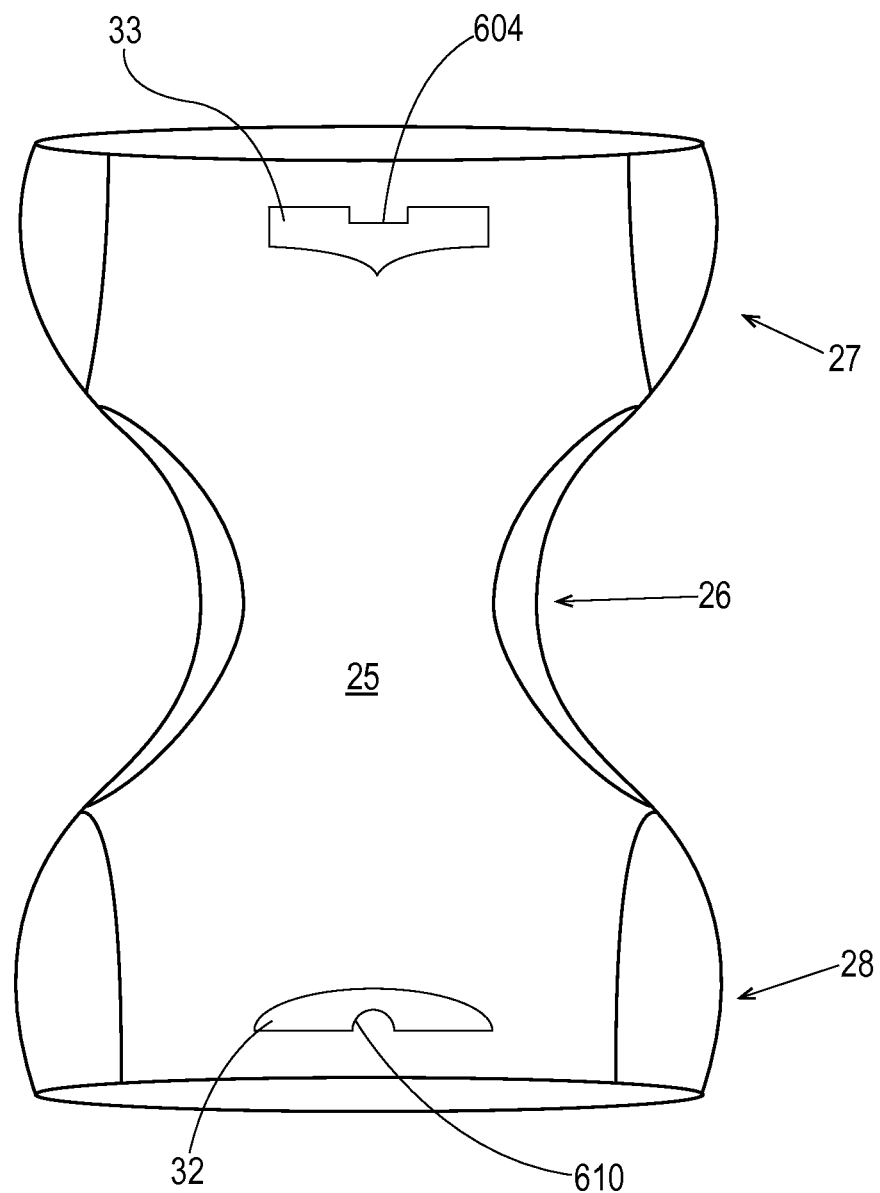

In an embodiment, the insert-gripping recesses 604 and 610 may have any suitable size, shape, area, and/or dimensions that allows a user to grasp a longitudinal outboard edge or portion, or other portion of the insert 50 and remove it from or apply it to the reusable outer cover 20. Stated another way, the insert-gripping recesses 604 and 610 permit portions of the longitudinal end areas of the insert 50 to be free of fastening to the insert fastener components 33 and 32 such that the insert 50 can easily be removed from and attached to the removable outer cover 20. In an embodiment, the insert-gripping recesses 604 and 610 may have an arcuate portion and/or a semi-circular portion. In other instances, the insert-gripping recesses 604 and 610 may form a semi-circular shape, a triangular shape, a rectangular shape, a square shape, and/or any other suitable shape or portion of a shape. Some example shapes of insert-gripping recesses 604 and 610 formed in insert fastener components 33 and 32 are illustrated in FIGS. 14-16. It is within the scope of the present disclosure to have any suitably shaped insert fastener components with any suitably shaped insert-gripping recesses formed therein. An example insert 50 is illustrated in dash on the removable outer cover 20 in FIG. 15. The insert 50 comprises fastener components 56 and 57 that removably attach to the insert fastener components 33 and 32 on the reusable outer cover 20. In the example embodiment of FIG. 15, it can be see how the insert-gripping recesses 604 and 610 provide an area for a user to grasp the insert 50 proximate to the longitudinal ends of the insert 50. These insert-gripping areas are indicated by arrow A in the front waist region 27 and arrow B in the rear waist region 28.

The insert-gripping recesses 604 and 610 may have any suitable areas and/or dimensions. In some example embodiments, the insert-gripping recesses 604 and 610 may have areas in the range of 0.1 square inch to 6 square inches, specifically reciting all 0.1 square inch increments within the specified ranges and all ranges formed therein or thereby. The insert-gripping recesses 604 and 610 may have maximum lateral widths measured parallel to the lateral axis 45 in the range of 0.4 inches to 5 inches or 0.5 inches to 3 inches, specifically reciting all 0.1 inch increments within the specified ranges and all ranges formed therein or thereby. The insert-gripping recesses 604 and 610 may have maximum longitudinal lengths measured parallel to the longitudinal axis 46 in the range of 0.4 inches to 5 inches or 0.5 inches to 3 inches, specifically reciting all 0.1 inch increments within the specified ranges and all ranges formed therein or thereby. The lateral width and/or the longitudinal length of the insert-gripping recesses 604 and 610 may be constant or variable throughout the recesses. In an embodiment, the lateral width and/or the longitudinal length of the insert-gripping recess 604 may be the same, substantially the same, or different than the lateral width and/or the longitudinal length of the insert-gripping recess 610. In an embodiment, the maximum lateral width may be measured along the first ends 600 and 606 in a direction parallel to the lateral axis 45 and the maximum longitudinal length may be measured in a direction parallel to the longitudinal axis 46. In some embodiments, the areas and/or dimensions of the insert-gripping recesses 604 and 610 may vary based on the size, areas, shapes, and/or dimensions of the insert fastener components 33 and 32 and/or the size, areas, shapes, and/or dimensions of the fastener components on the insert 50.

In an embodiment, referring to FIG. 17, the reusable outer cover 20 comprises a front waist region 27, a rear waist region 28, and a crotch region 26 positioned intermediate the front waist region 27 and the rear waist region 28. The reusable outer cover 20 may comprise a first insert fastener component 33 in the front waist region 27, a second insert fastener component 32 in the rear waist region, and a third insert fastener component 34 in the crotch region 26. The first, second, and third insert fastener components 33, 32, and 34 may have any suitable size, shape, area, dimensions, and/or configuration. The size, shape, area, dimensions, and/or configurations of the first and second insert fastener components 33 and 32 may be the same, substantially the same, or different. Each insert fastener component 33, 32, 34 may be configured to engage fastener components on the insert 50, as will be described in greater detail below. More than three insert fastener components may be provided in various embodiments. In an embodiment, at least two of the insert fastener components may be connected to each other.

In an embodiment, referring to FIG. 18, a disposable absorbent insert 50 may be configured to be engaged with the reusable outer covers 20 of the present disclosure to form the wearable absorbent article 10. The insert 50 may comprise a forward region 54, a rearward region 55, and a crotch region 99 disposed intermediate the forward region 54 and the rearward region 55. The forward region 54 generally aligns with the front waist region 27, the rearward region generally aligns with the rear waist region 28, and the crotch region 99 generally aligns with the crotch region 26 when the insert 50 is engaged with or joined to the reusable outer cover 20. The forward region 54 may comprise a first fastener component 56, the rearward region 55 may comprise a second fastener component 57, and the crotch region 99 may comprise a third fastener component 58. The first fastener component 56 may be configured to be joined to the first insert fastener component 33, the second fastener component 57 may be configured to be joined to the second insert fastener component 32, and the third fastener component 58 may be configured to be joined to the third insert fastener component 34 to join the disposable absorbent insert 50 to the reusable outer cover 20. Any suitable number of fastener components may be provided on the insert 50. In an embodiment, at least two of the fastener components may be connected to each other.

In an embodiment, the first insert fastener component 33 and the first fastener component 56 may together form a self-aligning fastener, a discrete fastener, and/or an adjustable fastener. The second insert fastener component 32 and the second fastener component 57 may together form a self-aligning fastener, a discrete fastener, and/or an adjustable fastener. The third insert fastener component 34 and the third fastener component 58 may together form a self-aligning fastener, a discrete fastener, and/or an adjustable fastener. The definitions for self-aligning, discrete, and adjustable fasteners appear above. In an embodiment, one side of a self-aligning fastener may be a magnet and the other side of the self-aligning fastener may be a magnet and/or a magnetically attractable material. The insert fastener components 33 and 32 of FIG. 17 may also comprise insert-gripping recesses 604 and 610 defined therein, as illustrated in dash in FIG. 17.

In various embodiments, the third fastener component 58 and the third insert fastener component 34 may together form a discrete fastener and/or a self-aligning fastener to allow a user to join to the insert 50 to the reusable outer cover 20 when the insert 50 is folded at least partially about its lateral axis 45 and the reusable outer cover 20 is in pant form as illustrated in FIG. 1C. This feature makes attachment of the insert 50 to the reusable outer cover 20 easy and causes alignment of the insert 50 with the reusable outer cover 20 at least in the crotch regions 26 and 99. In such an embodiment, the first fastener component 56 and the first insert fastener component 33 may be an adjustable fastener or a discrete fastener and, likewise, the second fastener component 57 and the first insert fastener component 32 may be an adjustable fastener or a discrete fastener. Such a feature provides a caregiver with the ability to suitably position the forward and rearward regions 54 and 55 in the front and rear waist regions 27 and 28 such that the insert 50 is comfortable to a wearer and retains bodily exudates within the insert 50. Any other suitable configurations of the self-aligning, discrete, and adjustable fasteners on the reusable outer covers 20 and the insert 50 are within the scope of the present disclosure. In an embodiment, the three fastener component pair may all be self-aligning fasteners, discrete fasteners, or adjustable fasteners. In an embodiment, more than three fastener component pairs may be present when the insert 50 is joined to the reusable outer cover 20.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. A wearable absorbent article comprising:
    a reusable outer cover comprising:
        a front waist region;
        a rear waist region;
        a crotch region disposed intermediate the front waist region and the rear waist region;
        a waist opening edge;
        a generally planar first insert fastener component in the front waist region proximate to the waist opening edge, wherein the first insert fastener component comprises a first end positioned most proximate to the waist opening edge and a second end positioned most distal from the waist opening edge, and wherein an insert-gripping recess is defined into the first end of the first insert fastener component and has at least a portion that extends from the first end of the first insert fastener component toward the second end of the first insert fastener component; and
        a second insert fastener component in the rear waist region proximate to the waist opening edge; and
    a disposable absorbent insert comprising:
        a forward region;
        a rearward region;
        a crotch region disposed intermediate the forward region and the rearward region;
        a first fastener component in the forward region configured to be joined to the first insert fastener component to attach the insert to the reusable outer cover; and
        a second fastener component in the rearward region configured to be joined to the second insert fastener component to attach the insert to the reusable outer cover.

2. The wearable absorbent article of claim 1, wherein the wearable absorbent article forms a pant.

3. The wearable absorbent article of claim 1, wherein the second insert fastener component comprises a first end positioned most proximate to the waist opening edge and a second end positioned most distal from the waist opening edge,— wherein a second insert-gripping recess is defined into the first end of the second insert fastener component, and wherein the second insert fastener component is positioned on a wearer-facing surface of the reusable outer cover.

4. The wearable absorbent article of claim 1, wherein the reusable outer cover comprises a third insert fastener component positioned in the crotch region, wherein the disposable absorbent insert comprises a third fastener component positioned in the crotch region configured to be joined to the third insert fastener component to attach the insert to the reusable outer cover.

5. The wearable absorbent article of claim 4, wherein the third insert fastener component and the third fastener component together form a self-aligning fastener.

6. The wearable absorbent article of claim 5, wherein the first insert fastener component and the first fastener component together form a discrete fastener.

7. The wearable absorbent article of claim 5, wherein the second insert fastener component and the second fastener component together form a discrete fastener.

8. The wearable absorbent article of claim 5, wherein the first insert fastener component and the first fastener component together form a self-aligning fastener.

9. The wearable absorbent article of claim 5, wherein the second insert fastener component and the second fastener component together form a self-aligning fastener.

10. The wearable absorbent article of claim 4, wherein the third insert fastener component and the third fastener component together form a discrete fastener.

11. The wearable absorbent article of claim 10, wherein the first insert fastener component and the first fastener component together form an adjustable fastener.

12. The wearable absorbent article of claim 10, wherein the second insert fastener component and the second fastener component together form an adjustable fastener.

13. The wearable absorbent article of claim 1, wherein the recess comprises an arcuate portion, and wherein the insert-gripping recess has a lateral width along the first end in the range of 0.5 inches to 3 inches.

14. The wearable absorbent article of claim 1, wherein the first end of the first insert fastener component extends in a direction generally parallel to a lateral axis of the reusable outer cover in areas of the first end that are free of the insert-gripping recess.

15. The wearable absorbent article of claim 1, wherein the second end of the first insert fastener component generally forms a straight line.

16. A wearable absorbent article comprising:
a reusable outer cover comprising:
a front waist region;
a rear waist region;
a crotch region disposed intermediate the front waist region and the rear waist region;
a first insert fastener component in the front waist region;
a generally flat second insert fastener component in the rear waist region, wherein an insert-gripping recess is defined into a first end of the second insert fastener component, and wherein the insert-gripping recess extends from the first end of the second insert fastener component that is positioned proximate to a waist edge opening of the reusable outer cover toward a lateral axis of the reusable outer cover; and
a third insert fastener component in the crotch region; and
a disposable absorbent insert comprising:
a forward region;
a rearward region;
a crotch region disposed intermediate the forward region and the rearward region;
a first fastener component in the forward region configured to be joined to the first insert fastener component;
a second fastener component in the rearward region configured to be joined to the second insert fastener component; and
a third fastener component in the crotch region configured to be joined to the third insert fastener component, wherein the third insert fastener component and the third fastener component together form a self-aligning fastener.

17. The wearable absorbent article of claim 16, wherein the first insert fastener component and the first fastener component together form a discrete fastener.

18. The wearable absorbent article of claim 17, wherein the second insert fastener component and the second fastener component together form a discrete fastener.

19. The wearable absorbent article of claim 16, wherein the third insert fastener component comprises a magnet, and wherein the third fastener component comprises a magnetically attractable material.

20. The wearable absorbent article of claim 16, wherein the first insert fastener component comprises an insert-gripping recess defined therein, and wherein the first insert fastener component is positioned on a wearer-facing surface of the reusable outer cover.

21. The wearable absorbent article of claim 20, wherein the first insert fastener component and the first fastener component together form a self-aligning fastener, and wherein the second insert fastener component and the second fastener component together form a self-aligning fastener.

22. A wearable absorbent article comprising:
a reusable outer cover comprising:
a front waist region;
a rear waist region;
a crotch region disposed intermediate the front waist region and the rear waist region;
a first insert fastener component in the front waist region;
a second insert fastener component in the rear waist region; and
a third insert fastener component in the crotch region; and
a disposable absorbent insert comprising:
a forward region;
a rearward region;
a crotch region disposed intermediate the forward region and the rearward region;
a first fastener component in the forward region configured to be joined to the first insert fastener component, wherein the first insert fastener component and the first fastener component together form a self-aligning fastener;
a second fastener component in the rearward region configured to be joined to the second insert fastener component, wherein the second insert fastener component and the second fastener component together form a self-aligning fastener; and
a third fastener component in the crotch region configured to be joined to the second insert fastener component, wherein the third insert fastener component and the third fastener component together form a discrete fastener;
wherein the first insert fastener component or the second insert fastener component has an insert-gripping recess extending into a first edge of the first or second insert fastener components.

* * * * *